(12) United States Patent
Lehmann et al.

(10) Patent No.: US 7,803,960 B2
(45) Date of Patent: Sep. 28, 2010

(54) PHENYLOXYANILINE DERIVATIVES

(75) Inventors: Lutz Lehmann, Berlin (DE); Axel Rother, Berlin (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 11/896,607

(22) Filed: Sep. 4, 2007

(65) Prior Publication Data
US 2008/0177108 A1    Jul. 24, 2008

Related U.S. Application Data

(60) Provisional application No. 60/842,024, filed on Sep. 5, 2006.

(30) Foreign Application Priority Data
Sep. 4, 2006   (EP)   .................................. 06018455

(51) Int. Cl.
*C07C 309/00* (2006.01)
(52) U.S. Cl. ..................................................... 558/49

(58) Field of Classification Search ....................... None
See application file for complete search history.

(56) References Cited

U.S. PATENT DOCUMENTS 6,870,069 B2 *   3/2005   Suzuki et al.   ............... 564/221
2004/0138310 A1   7/2004   Suzuki et al.

OTHER PUBLICATIONS

Solomons, Organic Chemistry, 5th Edition, 1992, John Wiley & Sons, Inc., New York, pp. 240-243.*
Zhang M-R et al, "Development of a New Radioligand, N-(5-fluoro-2-phenoxyphenyl)-N-(2-A 18Fufluoroethyl-5-methoxybenzyl)acetamide, for PET Imaging of Peripheral Benzodiazepine Receptor in Primate Brain", Journal of Medicinal Chemistry, American Chemical Society. Washington, US, vol. 47 No. 9, Apr. 22, 2004, pp. 2228-2235.

* cited by examiner

*Primary Examiner*—Paul A Zucker
(74) *Attorney, Agent, or Firm*—Millen, White, Zelano & Branigan, P.C.

(57) ABSTRACT

The present invention relates to phenyloxyaniline derivatives, to methods of their production and to uses thereof.

6 Claims, 10 Drawing Sheets

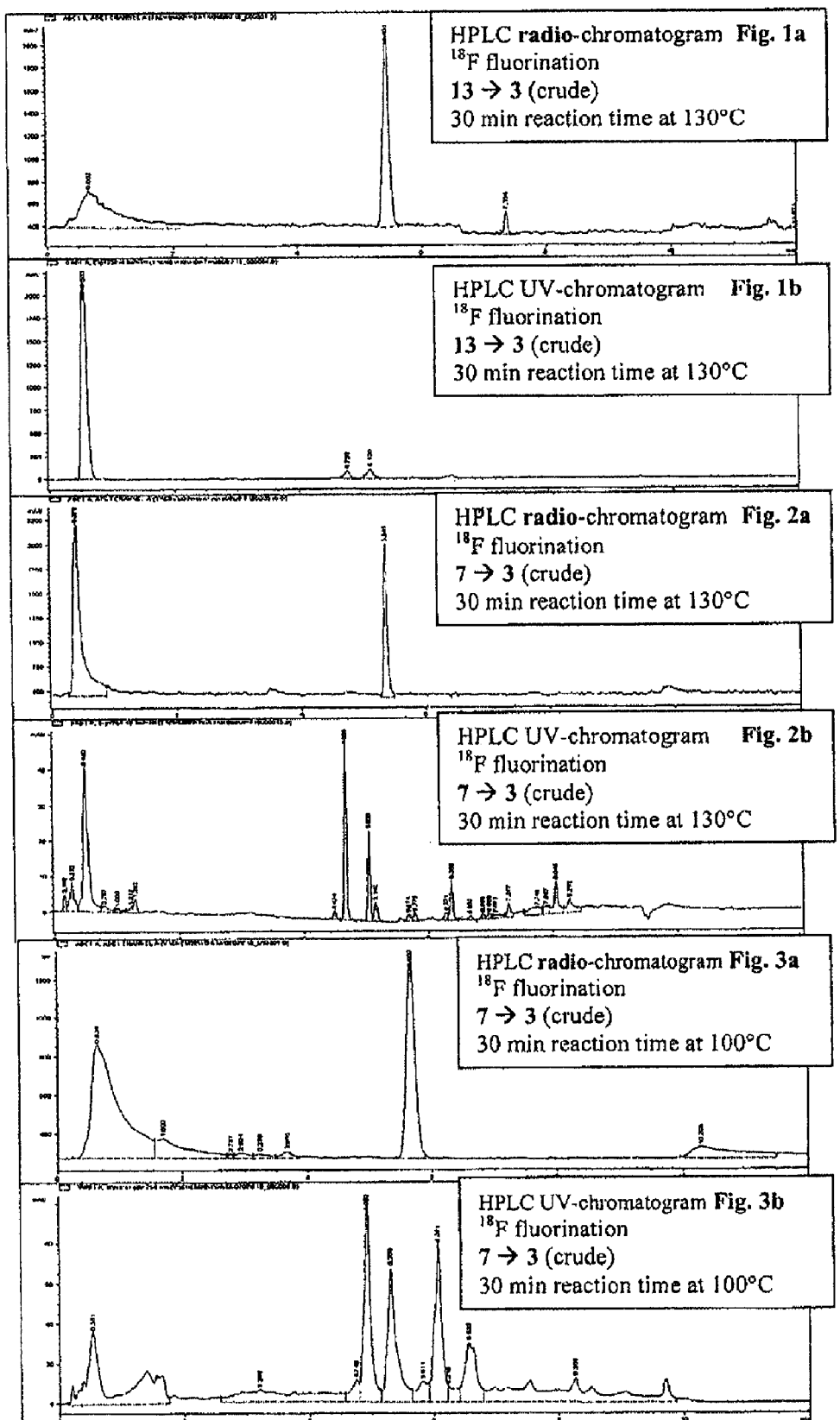

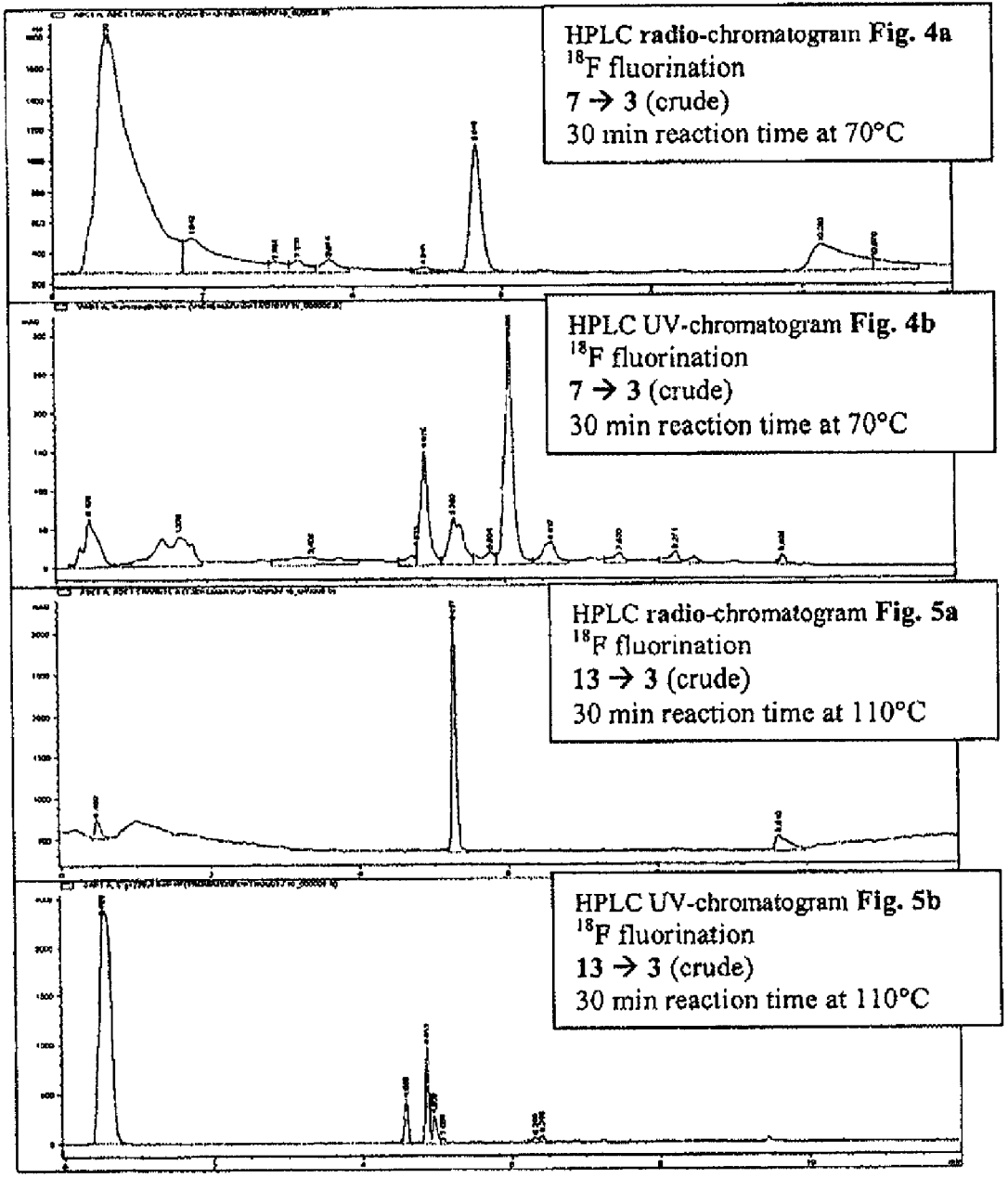

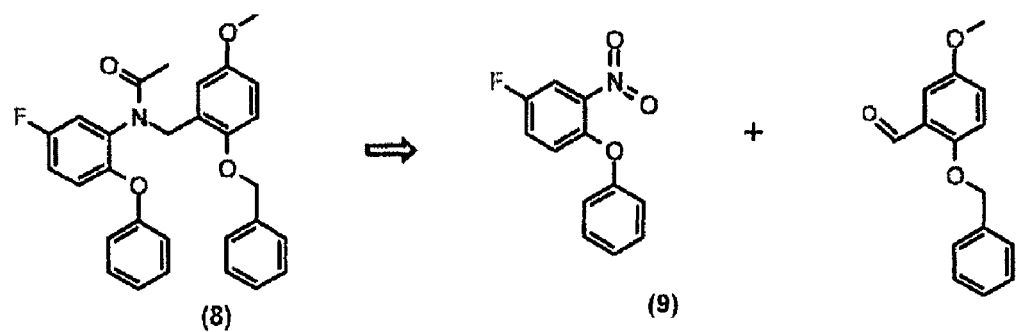
Figure 10
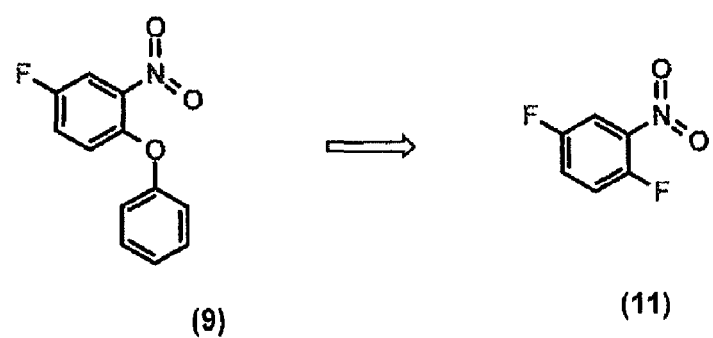
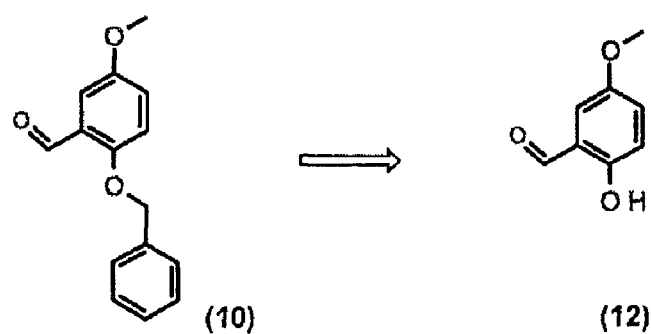
Figure 11

PHENYLOXYANILINE DERIVATIVES

This application claims the benefit of the filing date of U.S. Provisional Application Ser. No. 60/842,024 filed Sep. 5, 2006, which is incorporated by reference herein.

BACKGROUND ART

Peripheral benzodiazepine receptor (PBR) is expressed in most organs and its expression is reported to be increased in activated microglia in the brain which are the smallest type of glial cells acting as the immune cells of the central nervous system (CNS). Microglia are related to other phagocytic cells including macrophages and dendritic cells. Microglia are thought to be highly mobile cells that play numerous important roles in protecting the nervous system. They are also thought to play a role in neurodegenerative disorders such as Alzheimer's disease, dementia, multiple sclerosis and Amyotrophic lateral sclerosis. Microglia are responsible for producing an inflammatory reaction to insults (*J. Neuroinflammation*, 2004, Jul 30; 1(1):14.), The C-11 isotope labeled version of PK11195 (1) has been widely used for the in vivo imaging of neuroinflamation and PBRs, but its signal in the brain was not high enough for stable quantitative analysis.

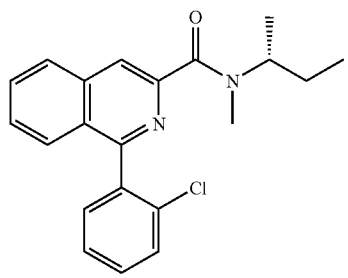

(1)

Furthermore, it has been shown that the development of superior positron-emitting ligands, like [$^{11}$C]DAA1106 (2) (e.g. Eur J. Pharmacol. 1999 Apr. 29; 371(2-3):197-204 and Life Sci. 1999; 64(16):1455-64) and [$^{18}$F]fluoroethyl-DAA1106 (3) (e.g. J. Nucl. Med., (2006), 47, 43-50), for visualization of PBRs is possible: The compounds 2 and 3 have a higher binding affinity to PBR and a higher accumulation in the brain than [$^{11}$C]PK11195 (1).

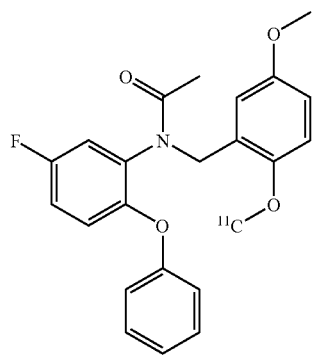

(2)

-continued

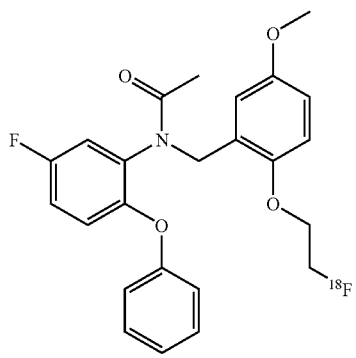

(3)

The non-radioactive version of compound 2 is claimed by the patent family related to WO99/006353, whereas the compound 3 is claimed by the patent family related to U.S. Pat. No. 6,870,069.

Compound 3 can be synthesized by the alkylation reaction of the phenol DAA1123 (4) with [$^{18}$F]-1-bromo-2-fluoro-ethane (5) as shown in FIG. 6. The drawback of the reaction is that the reagent [$^{18}$F]-1-bromo-2-fluoro-ethane (5) has to be synthesized from trifluoro-methanesulfonsäure-2-bromo-ethyl ester (6) prior phenol alkylation (4→3). Due to the fact that the $^{18}$F isotope has a half-life of only 111 min it is a challenge to produce [$^{18}$F]-1-bromo-2-fluoro-ethane (5) just in time and to carry out the subsequent alkylation in good yield. The overall radiochemical yield for this two-step sequence shown in FIG. 6 is normally lower than 10% yield.

Attempts have been made to synthesize compound 3 directly by starting from tosylate 7 (J. Med. Chem., (2004), 2228) by $^{18}$F labeling in a one-step procedure, (see FIG. 7). The reaction was carried out between 80° C. and 120° C. However, the radiochemical yields were not reproducible (2%-60%). In addition purification of [$^{18}$F]-(3) from reaction mixture was often difficult since many of the impurities resulting from the target and reaction greatly reduced the efficiency (J. Med. Chem., (2004), 2228).

It is known from literature (Biorg. Med. Chem., (2004), 12, 423) that compound 7 can be prepared from 4 by alkylation of 1,2-bis-tosyloxy-ethane which is commercially available (see FIG. 8).

Compound 4 is prepared from benzyl ether 8 by catalytic hydrogenation (see FIG. 9). Benzyl ether 8 is prepared in a one-pot reaction from nitro compound 9 and aldehyde 10 (see FIG. 10) Nitro compound 9 is synthesized from difluoride (11) and phenol by nucleophilic aromatic substitution reaction. Whereas compound 10 is prepared from phenol 12 and benzyl bromide (see FIG. 11) It would be useful to have a practical and sufficient technique for the synthesis of $^{18}$F-(3) in only one rather than in two radiochemical steps, The profile of by-products needs to be simple enough so that the desired product $^{18}$F-(3) can be purified easily, In addition it would be useful to have convenient synthetic routes to compounds and intermediates which allow the one-step labeling towards 18F-(3).

SUMMARY OF INVENTION

The present invention provides novel compounds of Formula I.

The present invention provides novel compounds of Formula II.

The invention further provides a novel process of preparing N-(5-Fluoro-2-phenoxyphenyl)-N-(5-methoxy-2-(2-tosyloxy-ethoxy)-benzyl)acetamide (7) and compounds represented by Formula I or II The invention further provides a novel process of preparing N-(5-Fluoro-2-phenoxyphenyl)-N-(2-(2-[$^{18}$F]fluoroethoxy)-5-methoxybenzyl)acetamide (3).

BRIEF DESCRIPTION OF DRAWINGS

FIG. 1a: Depicts a HPLC radio-chromatogram 18F fluorination of a compound of the invention.

FIG. 1b: Depicts a HPLC radio-chromatogram 18F fluorination of a compound of the invention.

FIG. 2a: Depicts a HPLC radio-chromatogram 18F fluorination of a compound of the invention.

FIG. 2b: Depicts a HPLC radio-chromatogram 18F fluorination of a compound of the invention.

FIG. 3a: Depicts a HPLC radio-chromatogram 18F fluorination of a compound of the invention.

FIG. 3b: Depicts a HPLC radio-chromatogram 18F fluorination of a compound of the invention.

FIG. 4a: Depicts a HPLC radio-chromatogram 18F fluorination of a compound of the invention.

FIG. 4b: Depicts a HPLC radio-chromatogram 18F fluorination of a compound of the invention.

FIG. 5a: Depicts a HPLC radio-chromatogram 18F fluorination of a compound of the invention.

FIG. 5b: Depicts a HPLC radio-chromatogram 18F fluorination of a compound of the invention.

FIG. 10: Depicts the synthesis of Benzyl ether 8 in a one-pot reaction from nitro compound 9 and aldehyde 10.

FIG. 11: Depicts the synthesis of Nitro compound 9 from difluoride (11) and phenol by nucleophilic aromatic substitution reaction and the preparation of compound 10 from phenol 12 and benzyl bromide.

DETAILED DESCRIPTION OF THE INVENTION

Figure 6:
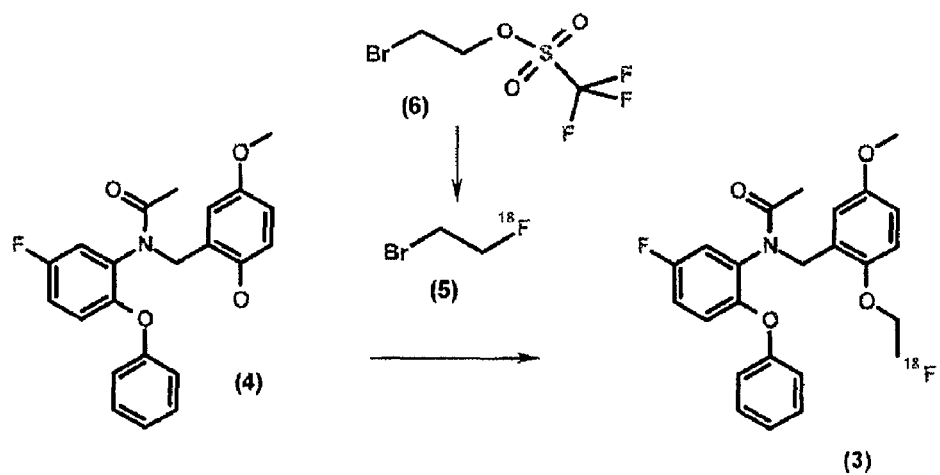
FIG. 6: Depicts the synthesis of Compound 3 by the alkylation reaction of the phenol DAA1123 (4) with [$^{18}$F]-1-bromo-2-fluoro-ethane (5).
Figure 7:
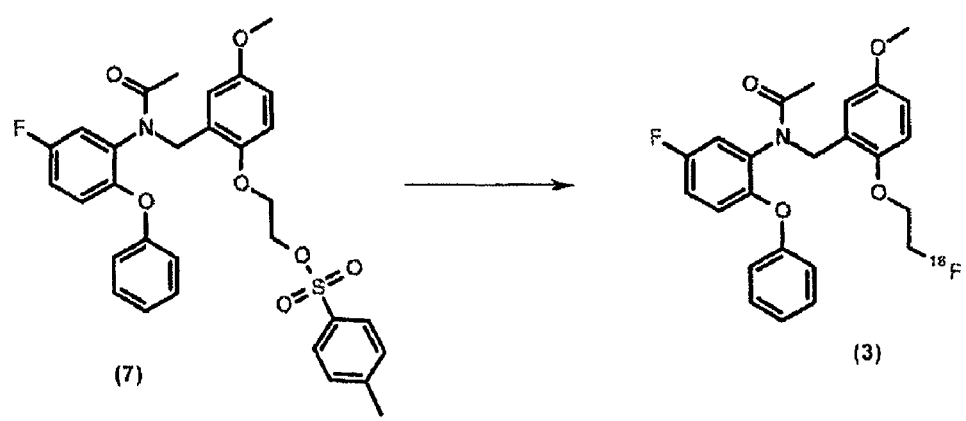
FIG. 7: Depicts the synthesis of compound 3 from tosylate 7.
Figure 8:
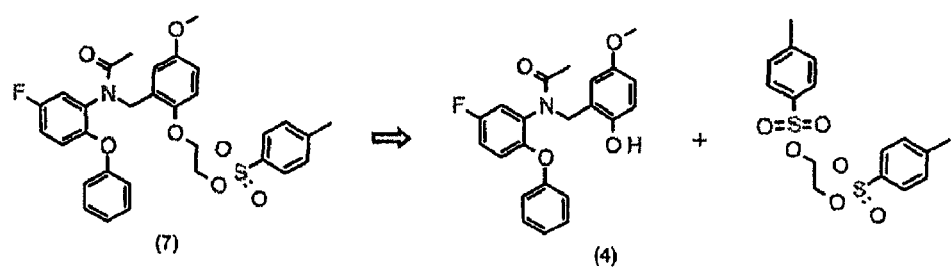
FIG. 8: Depicts the synthesis of compound 7 from compound 4

In a first aspect the present invention is directed to compounds of formula I:

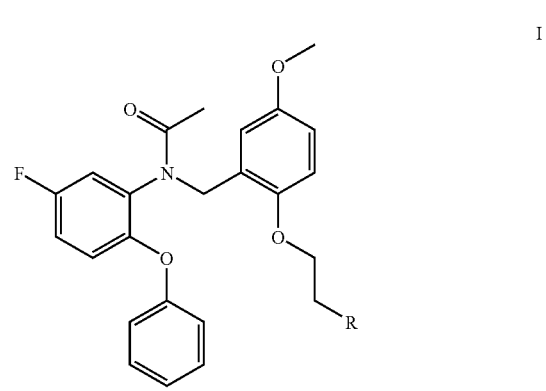

wherein
R is
a) —OS(O)$_2$-L,
b) chloro,
c) bromo or
d) iodo.
In preferred embodiments of compounds of Formula I,
R is
a) —OS(O)$_2$-L
b) bromo or
c) chloro.
In further preferred embodiments of compounds of Formula I,
R is
a) —OS(O)$_2$-L, or
b) bromo.
L is
a) branched or unbranched alkyl
b) perhalo alkyl
c) aralkyl
d) alkyl-phenyl
e) (di-alkyl)-phenyl
f) (tri-alkyl)-phenyl
g) (alkoxy-phenyl)
h) (nitro-phenyl)
i) (halo-phenyl)
j) naphtyl or
k) heteroaryl
whereas L is not (para-methyl)-phenyl.
In preferred embodiments of compounds of Formula I,
L is
a) methyl
b) trifluormethyl
b) nonafluorobutyl
c) (nitro-phenyl)
d) (halo-phenyl)
e) C$_1$-C$_6$ alkylphenyl or
f) (2,4,6-C$_1$-C$_6$ trialkyl)phenyl whereas L is not (para-methyl)-phenyl.

In further preferred embodiments of compounds of Formula I,
L is
a) methyl
b) trifluormethyl or
c) nonafluorobutyl A preferred series of compounds of Formula I include mesyloxy and bromo derivatives having the following structures:

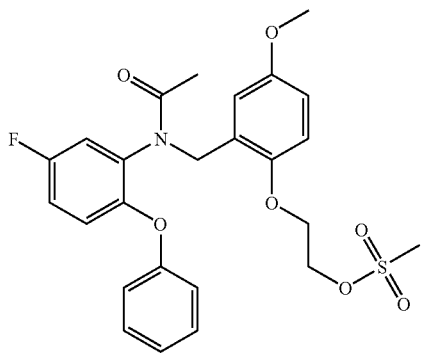

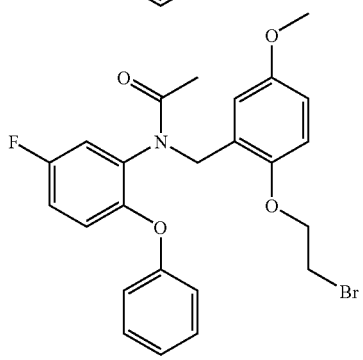

In a second aspect the present invention is directed to compounds of formula II which are possible starting materials of compounds of formula I:

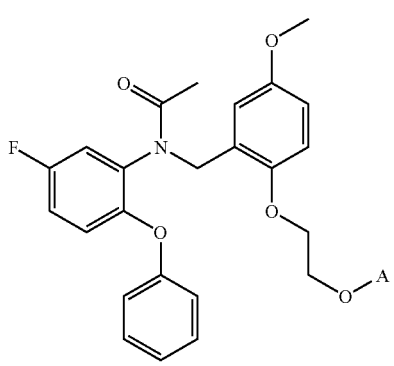

wherein
A is
a) hydrogen
b) $SiR^1_3$
c) $CH_2$-G
d) C(O)-Q
e) C(O)O-E f) —($R^2$-phenyl)
g) —(($R^2$)$_2$-phenyl)
h) tetrahydropyranyl
i) (1-alkoxy)-alkyl
j) (1-alkoxy)-cycloalkyl
k) allyl or
l) tert-butyl.

In preferred embodiments of compounds of Formula II
A is
a) hydrogen
b) $SiR^1_3$
c) $CH_2$-G
d) tetrahydropyranyl
e) allyl or
tent-butyl.

In further preferred embodiments of compounds of Formula II,
A is
a) hydrogen
b) $SiR^1_3$
c) $CH_2$-G
d) tetrahydropyranyl or
e) tert-butyl.

G is
a) phenyl
b) alkoxy
c) dimethoxyphenyl
d) nitrophenyl
e) halophenyl
f) di-halophenyl
g) cyanophenyl
h) p-biphenyl
i) acylaminophenyl
j) triphenyl
k) (methoxyphenyl)phenyl
l) di(methoxyphenyl)phenyl
m) α-naphtyldiphenyl or
n) hydrogen In preferred embodiments of compounds of Formula II,
G is
a) phenyl
b) methoxy
c) p-methoxyphenyl
d) p-nitrophenyl
e) p-chlorophenyl or
f) triphenyl.

In further preferred embodiments of compounds of Formula II
G is
a) phenyl
b) methoxy or
c) p-methoxyphenyl.

Q is
a) hydrogen
b) $C_1$-$C_5$ branched or unbranched alkyl
c) halomethyl
d) dihalomethyl
e) trihalomethyl
f) phenyl
g) biphenyl
h) triphenylmethoxymethyl or
i) phenoxymethyl.

In preferred embodiments of compounds of Formula II
Q is
a) hydrogen
b) methyl
c) phenyl or
d) phenoxymethyl.
In further preferred embodiments of compounds of Formula II,
Q is
a) is methyl
b) phenyl.
E is
a) lower branched or unbranched alkyl
b) methoxymethyl
c) vinyl
d) allyl
e) benzyl
f) methoxyphenyl
g) dimethoxyphenyl or
h) nitrophenyl
In preferred embodiments of compounds of Formula II,
E is
a) methyl
b) tert-butyl
c) methoxymethyl or
d) phenyl
In further preferred embodiments of compounds of Formula II,
E is
a) methyl
c) tert-butyl
b) phenyl
$R^1$ is independently from each other
a) lower branched or unbranched alkyl
b) phenyl or
c) benzyl and
In preferred embodiments of compounds of Formula II,
$R^1$ is independently from each other
a) methyl
b) ethyl
c) isopropyl
d) tert-butyl
e) phenyl or
f) benzyl
In further preferred embodiments of compounds of Formula II,
$R^1$ is independently from each other
a) methyl
b) ethyl
c) isopropyl
d) tert-butyl or
e) phenyl
$R^2$ is independently from each other
a) methoxy
b) nitro
c) halo or
d) cyano
In preferred embodiments of compounds of Formula II,
$R^2$ is independently from each other
a) methoxy
b) nitro
c) chloro
In further preferred embodiments of compounds of Formula II,
$R^2$ is independently from each other
a) methoxy
b) nitro A preferred series of compounds of Formula II include derivatives having the following structures:

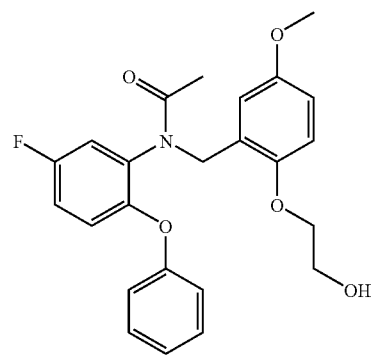

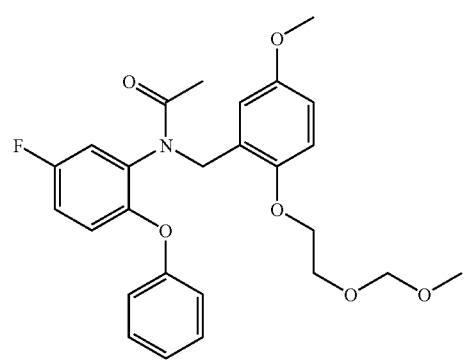

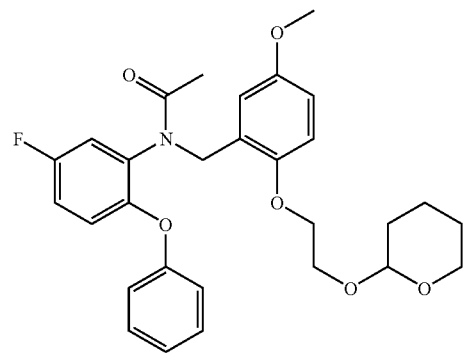

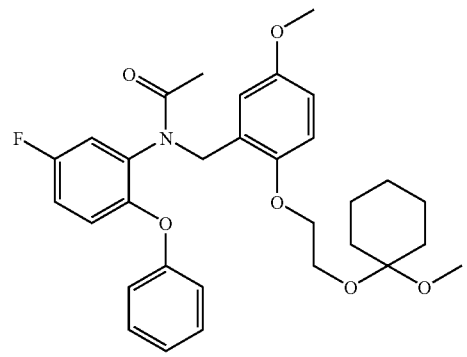

-continued

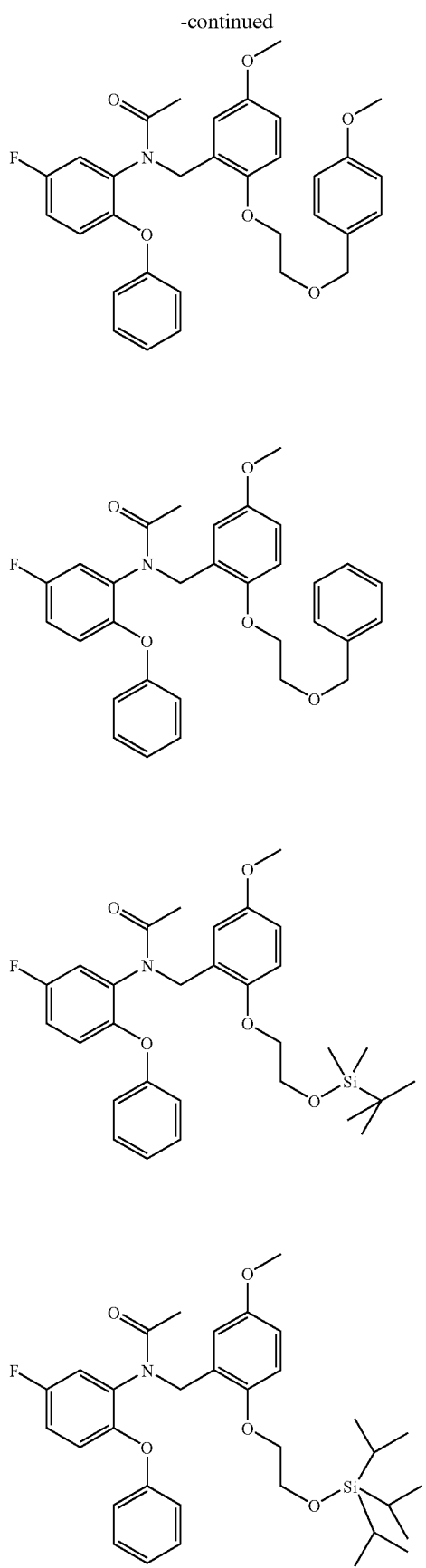

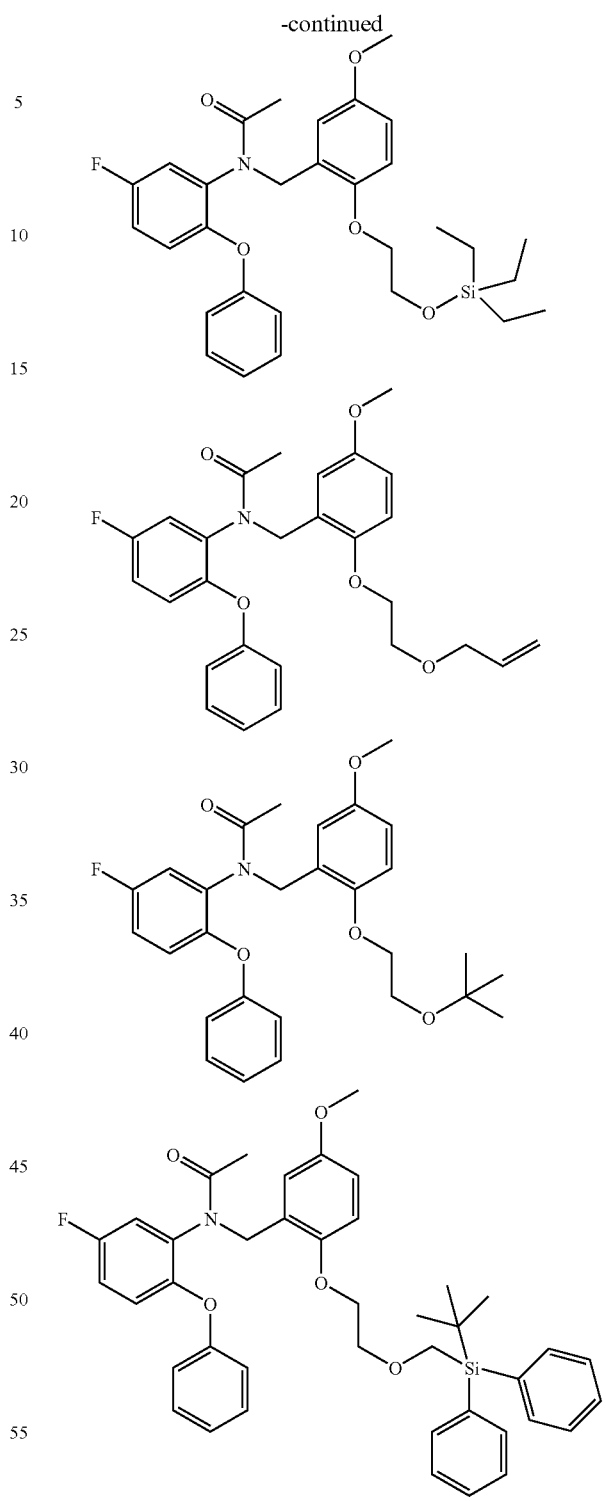

As used in the specification and appended claims unless specified to the contrary, the term "lower un-branched or branched alkyl" shall have the following meaning: a substituted or unsubstituted, straight or branched chain monovalent or divalent radical consisting substantially of carbon and hydrogen, containing no unsaturation and having from one to eight carbon atoms, e.g. but not limited to methyl, ethyl, n-propyl, n-pentyl, 1,1-dimethylethyl (t-butyl), n-heptyl, and the like.

The term "aryl" as employed herein by itself or as part of another group refers to monocyclic or bicyclic aromatic groups containing from 6 to 12 carbons in the ring portion, preferably 6-10 carbons in the ring portion, such as phenyl, naphthyl or tetrahydronaphthyl. The term "heteroaryl" as employed herein refers to groups having 5 to 14 ring atoms; 6, 10 or 14 Π (pi) electrons shared in a cyclic array; and containing carbon atoms and 1, 2, 3 or 4 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4aH-carbazolyl, carbazolyl, carbolinyl, phenanthridinyl, acridinyl, perimidinyl, phenanthrolinyl, phenazinyl, isothiazolyl, phenothiazinyl, isoxazolyl, furazanyl and phenoxazinyl groups).

If a chiral center or another form of an isomeric center is present in a compound according to Formula I or II of the present invention, all forms of such isomer, including enantiomers and diastereoisomers, are intended to be covered herein. Compounds containing a chiral center may be used as racemic mixture or as an enantiomerically enriched mixture or the racemic mixture may be separated using well-known techniques and an individual enantiomer may be used alone. In cases in which compounds have unsaturated carbon-carbon bonds double bonds, both the cis-isomer and trans-isomers are within the scope of this invention. In cases wherein compounds may exist in tautomeric forms, such as keto-enol tautomers, each tautomeric form is contemplated as being included within this invention whether existing in equilibrium or predominantly in one form.

In a third aspect the present invention is directed to a process for preparing N-(5-Fluoro-2-phenoxyphenyl)-N-(5-methoxy-2-tosyloxyethoxybenzyl)acetamide (7) or a compound represented by Formula I or II characterized by a) reductively N-alkylating a compound of formula III:

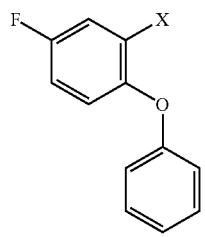

III with an aldehyde of formula IV

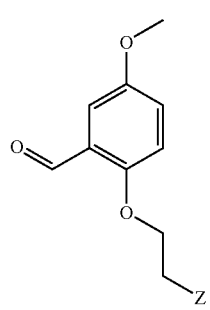

IV and subsequent N-acetylation, b) N-alkylating an aniline of formula V:

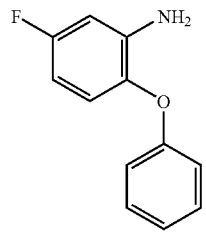

V with an electrophile of formula VI

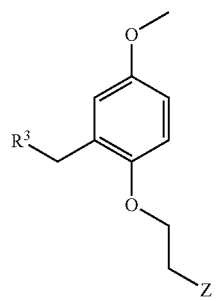

VI and subsequent N-acetylation, c) alkylation of phenol 4 with an

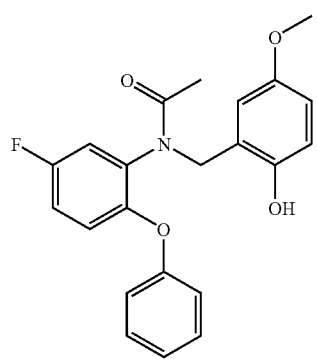

4 electrophile of formula VII

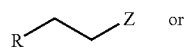

VII or d) N-alkylating of the compound of formula VIII

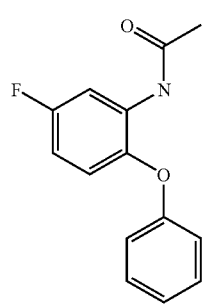

VIII with an electrophile of formula VI.
wherein
X is a) nitro or
b) amino and
Z is
a) R
b) tosyloxy or
c) O-A and
whereas R and A are above-defined.
In preferred embodiments of compounds of formula VII,
Z is
a) methanesulphonyloxy
b) trifluoromethansulphonyloxy
c) nonafluorobutanesulfonyloxy
d) tosyloxy
e) bromo
f) O-A
whereas A is above-defined.
In further preferred embodiments of compounds of formula VII,
Z is
a) methanesulphonyloxy
b) trifluoromethansulphonyloxy
c) nonafluorobutanesulfonyloxy
d) tosyloxy
e) bromo
f) hydroxyl
g) (tert-butyl dimethyl) silyloxy
h) (triisopropyl) silyloxy
i) phenyl
j) tetrahydropyranyl or
k) tert-butyl.
In further preferred embodiments of compounds of formula VII,
Z is
a) methanesulphonyloxy
b) trifluoromethansulphonyloxy
c) nonafluorobutanesulfonyloxy
d) tosyloxy
e) bromo
f) hydroxyl
g) (tert-butyl dimethyl) silyloxy
h) (triisopropyl) silyloxy
ii) phenyl-methyl)oxy
jj) (2-tetrahydropyranyl)oxy 1, or
kk) tert-butyloxy.
$R^3$ is
a) R or
b) tosyloxy
whereas R is above-defined.
In preferred embodiments of compounds of formula VI, $R^3$ is
a) R
whereas R is above-defined.

Figure 9:
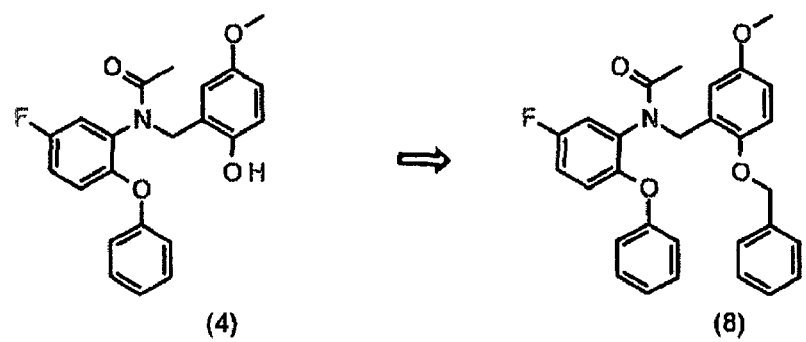
FIG. 9: Depicts the synthesis of Compound 4 from benzyl ether 8

The above mentioned processes of forming compound 7 or a compound of formula I and II avoid the laborious protecting group strategy as it is shown in FIGS. 9 and 11 and as it was reported e.g. in Biorg. Med. Chem., (2004), 12, 423. In this mentioned publication the phenol protecting "benzyl" has to be installed and deprotected within a relatively short sequence. The third aspect of the present invention provides a more convergent approach to synthesize a suited precursor for the later radiofluorination reaction.

A forth aspect of the invention is directed to a process of preparing compound 3 which is characterized by the nucleophilic $^{18}$F radiofluorination of compound 7 or a compound of formula I in only one radiochemical step. In contrast to the published one-step $^{18}$F labelling procedure (J. Med. Chem., (2004), 2228) the forth aspect of the present invention provides additional starting materials and/or new parameters which allow the $^{18}$F fluorination towards N-(5-Fluoro-2-phenoxyphenyl)-N-(2-(2-[$^{18}$F]fluoroethoxy)-5-methoxybenzyl) acetamide (3) without generating a disadvantageous amount of by-products which are costly or difficult to separate. The present invention comprises an approach for the nucleophilic $^{18}$F radiofluorination towards N-(5-Fluoro-2-phenoxyphenyl)-N-(2-(2-[$^{18}$F]fluoroethoxy)-5-methoxybenzyl)acetamide (3) which is characterized by use of starting materials represented by a) compound 7 and $^{18}$F anions which are reacted at temperatures in the range of from 121° C.-160° C. and, optionally, subsequent use of acid, or b) compounds of formula I and $^{18}$F anions which are reacted at temperatures in the range of from 50° C. to 160° C.

In preferred embodiments of $^{18}$F radiofluorinations towards N-(5-Fluoro-2-phenoxyphenyl)-N-(2-(2-[$^{18}$F]fluoroethoxy)-5-methoxybenzyl)acetamide (3) the reaction is characterized by use of starting materials represented by a) compound 7 and $^{18}$F anions which are reacted at temperatures in the range of from 121° C. to 150° C. and, optionally, subsequent use of mineral acids with concentrations between 0.5 N 6 N, or b) compounds of formula I and $^{18}$F anions which are reacted at temperatures in the range of from 75° C. to 150° C.

In further preferred embodiments of $^{18}$F radiofluorinations towards N-(5-Fluoro-2-phenoxyphenyl)-N-(2-(2-[$^{18}$F]fluoroethoxy)-5-methoxybenzyl)acetamide (3) the reaction is characterized by use of starting materials represented by a) compound 7 and $^{18}$F anions which are reacted at temperatures in the range of from 121° C. to 140° C., and, optionally, subsequent use of mineral acids with concentrations between 2 N-6 N, or b) compounds of formula I and $^{18}$F anions which are reacted at temperatures in the range of from 85° C. to 140° C.

The objects of the present invention are also solved by a process of preparing compound 3

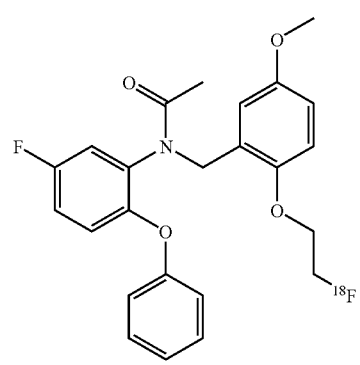

characterized by a) reacting compound 7

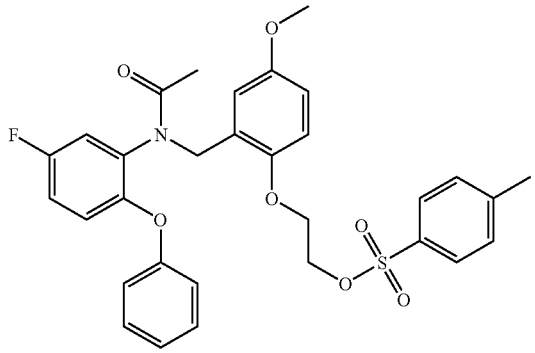

(7)

with $^{18}F$ anions, at temperatures in the range of from 121° C. to 160° C., and, optionally, upon obtainment of compound 3, addition of acid, or b) reacting a compound of formula I, as defined in any of claims 1-6 with $^{18}F$ anions at temperatures in the range of from 50° C. to 160° C.

In one embodiment, a) compound 7 is reacted with $^{18}F$ anions at temperatures in the range of from 121° C. to 150° C., and, optionally, upon obtainment of compound 3, at least one mineral acid having a concentration in the range of from 0.5N-6N is added, or b) a compound of formula I is reacted with $^{18}F$ anions at temperatures in the range of from 75° C. to 150° C.

Preferably, a) compound 7 is reacted with $^{18}F$ anions, at temperatures in the range of from 121° C. to 140° C. and, optionally, upon obtainment of compound 3, at least one mineral acid having a concentration in the range of 2N-6N is added, or b) a compound of formula I is reacted with $^{18}F$ anions at temperatures in the range of from 85° C. to 140° C.

In one embodiment in each of the reactions a) and b), the reaction with $^{18}F$ anions is conducted over a period in the range of from 1 to 60 minutes, preferably 5 to 50 minutes, more preferably 10 to 40 minutes.

The objects of the present invention are also solved by a composition comprising a compound according to Formula I, preferably as defined in any of claims 1-6, and a pharmaceutically acceptable carrier or diluent.

The objects of the present invention are furthermore solved by a kit comprising a sealed vial containing a compound according to Formula I, preferably as defined in any of claims 1-6, wherein, more preferably, said sealed vial contains a predetermined quantity of said compound.

The objects of the present invention are furthermore solved by a compound according to formula I, as defined in any of claims 1-6, for use as a pharmaceutical.

The objects of the present invention are furthermore solved by a use of a compound according to formula I, as defined in any of claims 1-6, for the manufacturing of a diagnostic imaging agent, wherein, preferably, said diagnostic imaging agent is for imaging diseases of the central nervous system.

The term "acid" as employed herein refers to mineral acids, including but not limited to acids such as hydrochloric, hydrobromic, hydroiodic, perchloric, phosphoric, carbonic, nitric or sulphuric acid or to appropriate organic acids which includes but not limited to acids such as aliphatic, cycloaliphatic, aromatic, araliphatic, heterocyclic, carboxylic and sulphonic acids, examples of which are formic, acetic, trifluoracetic, propionic, succinic, glycolic, gluconic, lactic, malic, fumaric, pyruvic, benzoic, anthranilic, mesylic, fumaric, salicylic, phenylacetic, mandelic, embonic, methansulfonic, ethanesulfonic, benzenesulfonic, phantothenic, toluenesulfonic and sulfanilic acid.

If, in the context of the process of preparing compound 3, the term "at least one mineral acid having a concentration in the range of form 0.5 N-6N" is used, this is meant to refer to a scenario, wherein the at least one mineral acid has a concentration in the indicated range. However, this term should also be understood as encompassing a scenario wherein more than one mineral acid is used, e.g. a mixture of several mineral acids, and the total acid concentration, i.e. the sum of all individual mineral acid concentrations is in the indicated range of from 0.5 N-6N.

The provision of $^{18}F$ anions is known to someone skilled in the art and in one embodiment is achieved by providing aqueous $H^{18}F$ to which a base, for example in the form of potassium carbonate or tetra alkyl ammonium carbonate is added. The aqueous $H^{18}F$ may be obtained from a synchrotron.

It is important that a radiofluorination causes as little by-products as possible in order to avoid a difficult purification of the desired product.

Figure 12:
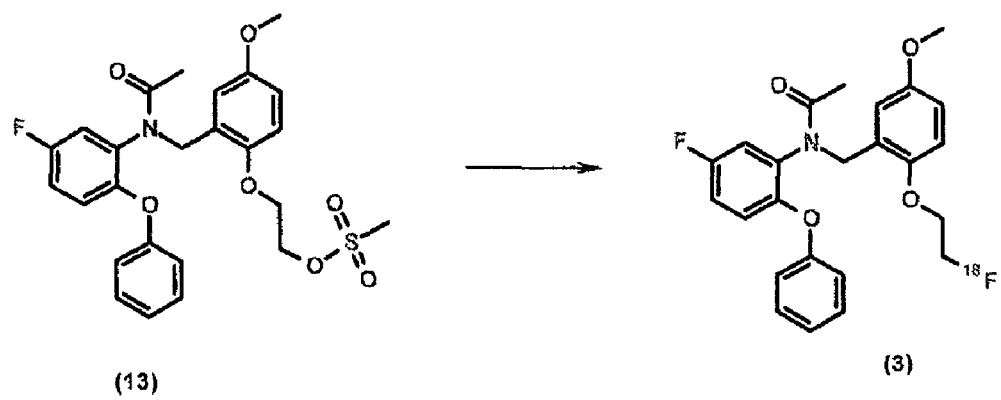
FIG. 12: Depicts the conversion of compound 13 to compound 3.

As depicted in FIG. 12 a compound of formula I, e.g. compound 13, can be radio-fluorinated to obtain the desired product 3 (see FIG. 1a). The reaction causes less non-radioactive by-products (see FIG. 1b) compared to a reaction in which compound 7 is converted to 3 at any temperature (compare FIG. 2b with 3b and 4b as example). Compound 7 as starting material shows surprisingly also an improved profile of by-products regarding radiofluorination by treatment with $^{18}F$ anion if the temperature is above 120° C. (compare FIG. 2b with 4b). If one compares the nucleophilic radiofluorination reaction of a compound of formula I with compound 7 it is obvious that radiofluorination of compounds of formula I can be conducted at all temperatures (see e.g. FIGS. 5a and 5b). The radiofluorination reaction can be carried out, for example in a typical reaction vessel (e.g. Wheaton vial) which is known to someone skilled in the art, or in a microreactor. The reaction can be heated by typical methods, e.g. oil bath, heating block or microwave. Furthermore it can be useful to add acid to the crude product or to the reaction mixture after the radiofluorinations of compound 7 or of compounds of formula I towards compound 3 has been carried out. The treatment with acid can lead surprisingly to an improved profile of by-products.

The radiofluorination reactions are carried out in dimethylformamide with potassium carbonate as base and "kryptofix" as crown-ether. But also other solvents can be used which are well known to experts. These possible conditions include, but are not limited to: dimethylsulfoxid and acetonitril as solvent and tetraalkyl ammonium and tertraalkyl phosphonium carbonate as base. Water and/or alcohol can be involved in such a reaction as co-solvent. The radiofluorination reactions are conducted for one to 60 minutes. Preferred reaction times are five to 50 minutes. Further preferred reaction times are 10 to 40 min.

Figure 13:
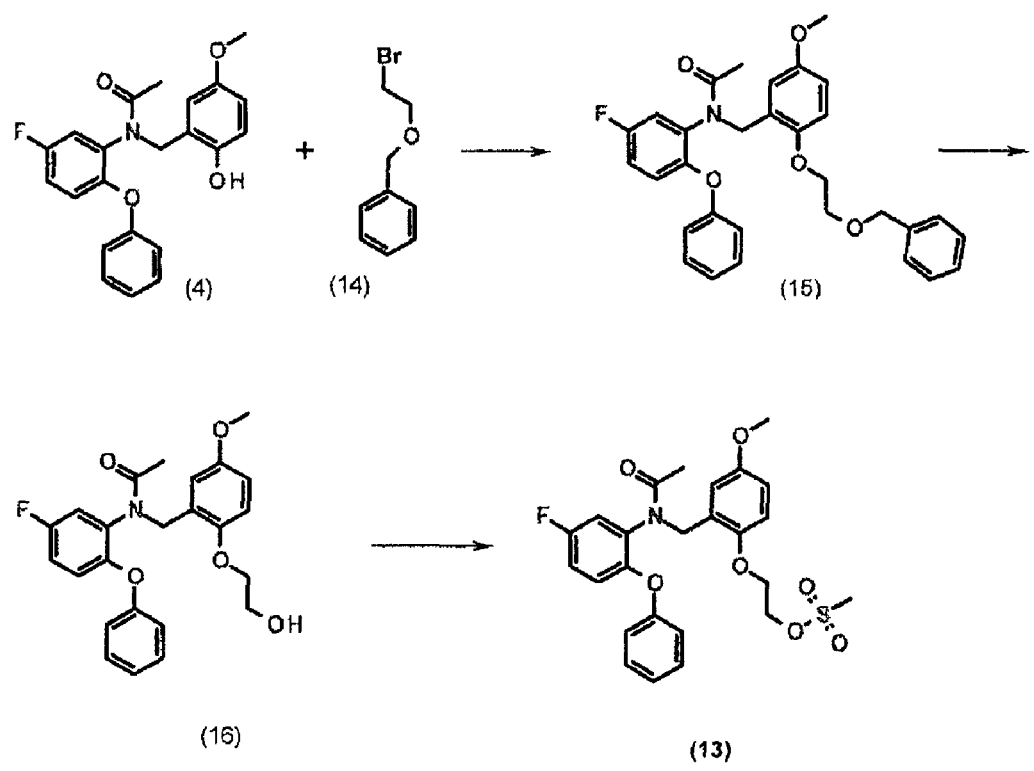
FIG. 13: Depicts an example of a synthetic route for forming a compound of Formula I via a compound of formula II.

FIG. 13 depicts an example of a synthetic route for forming a compound of formula I via a compound of formula II:

Compound 4 (J. Med. Chem.; 47; 9; (2004); 2228-2235) can be alkylated by use of e.g. benzyl protected bromoethanol (Bioorg. Med. Chem. Lett.; 15; 22; (2005); 4989-4993), potassium carbonate and sodium iodide in dimethylformamide to obtain ether 15. But also other bases, including but not limited to caesium or sodium carbonate, sodium hydroxid, potassium hydroxid, lithium hydroxid, tetra-alkyl hydroxid, sodium hydrid and other solvents, including but not limited to acetone, tetrahydrofuran, eventually mixed with water, are possible. Compound 15 is deprotected by heterogeneous catalysis and hydrogen. Suited reaction conditions are e.g. palladium on carbon and isopropanol. Other possible reagents and solvents for this kind of reaction of deprotection are known to experts and listed in T. Greene, "Protective Groups in Organic Synthesis", Wiley & Sons, 1999. The resulting alcohol 13 is then converted to compound 16 by use of e.g. mesylchloride, triethylamin and dichloromethane. Other possible solvents and bases including but not limited to, are dichloroethane, ethers, ethyl acetate, diisopropyl ethyl amine, DABCO ect.

Figure 14:
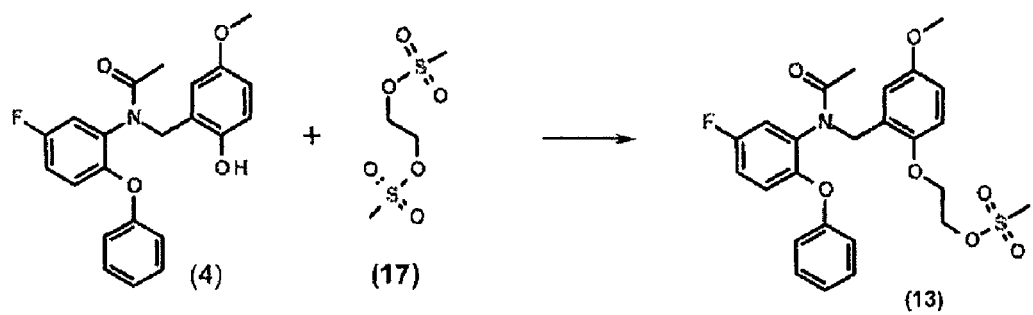
FIG. 14: Depicts an example of a synthetic route for forming a compound of Formula I.

FIG. 14 depicts another example of a synthetic route for forming a compound of Formula I. Phenol 4 can be alkylated by use of 1,2-bis-methanesulfonyloxy-ethane (J. Med. Chem.; 47; 17; (2004); 4300-4315), potassium carbonate and sodium iodide in dimethylformamide to obtain mesylate 13. But also other bases, including but not limited to caesium or sodium carbonate, sodium hydroxid, potassium hydroxid, lithium hydroxid, tetraalkyl hydroxid, sodium hydrid and other solvents, including but not limited to acetone, tetrahydrofuran, eventually mixed with water, are possible.

Figure 15:
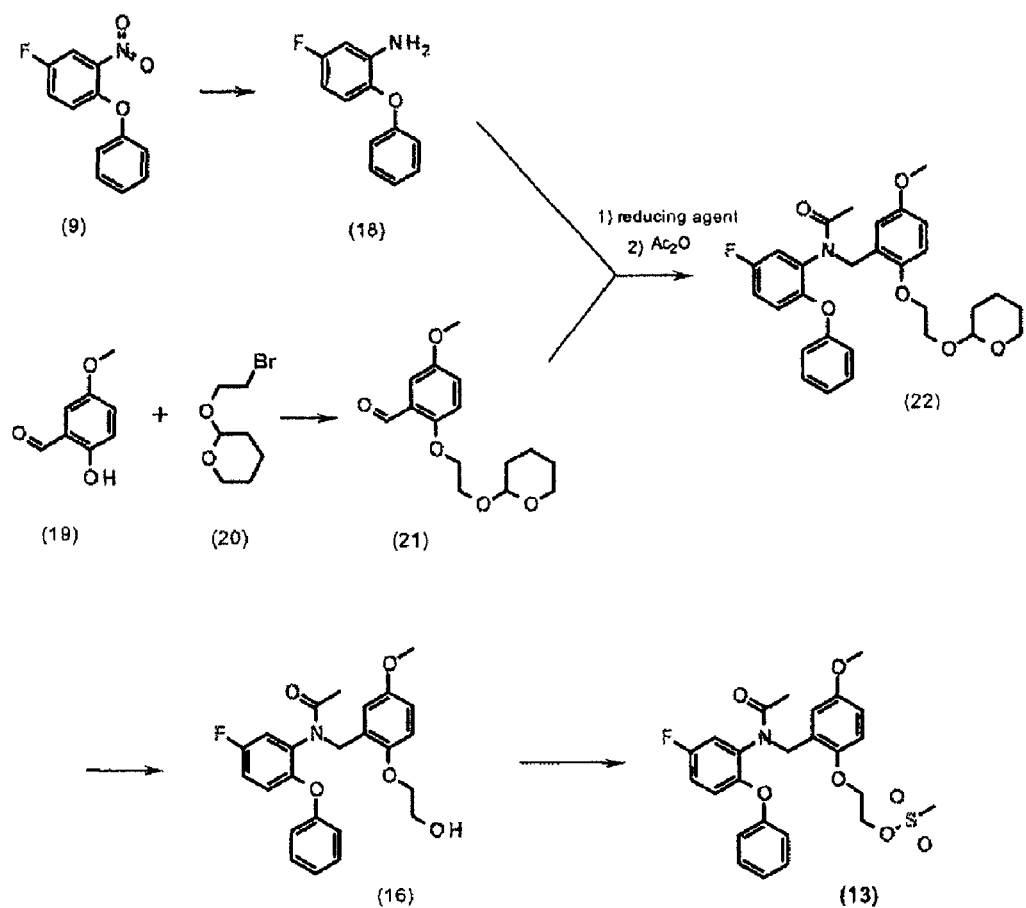
FIG. 15: Depicts an example of a synthetic route for reductively N-alkylation forming a compound of Formula I via a compound of formula III.

FIG. 15 depicts another example of a synthetic route for reductively N-alkylation forming a compound of Formula I via a compound of formula III:

Nitro-compound 9 is reduced to the corresponding aniline 18. A possible reducing agent for this reaction is hydrogen with palladium on carbon. Aniline 18 is converted in a reductive amination reaction with tris-acetoxy sodium borohydrid in dichloromethane and aldehyde 21 and subsequent acetylation with aceticacid anhydride to obtain the acetylated secondary aniline 22. Other useful reducing agents are well-known to experts: e.g. sodium cyano borohydrid in methanol or hydrogen and heterogenous catalysts (e.g. palladium on carbon (Bioorg. Med. Chem. Lett.; 15; 22; 2005; 4989-4993) or platinum oxide), dibutyl tin chloride and phenyl silane (Org. Lett; 25; 2005; 5653-5656). Deprotection of the tetrahydropyranyl ether 22 under acidic conditions with tosyl acid in methanol resulted in alcohol 16. The subsequent mesylation towards compound 13 has already been described in FIG. 13.

Figure 16:
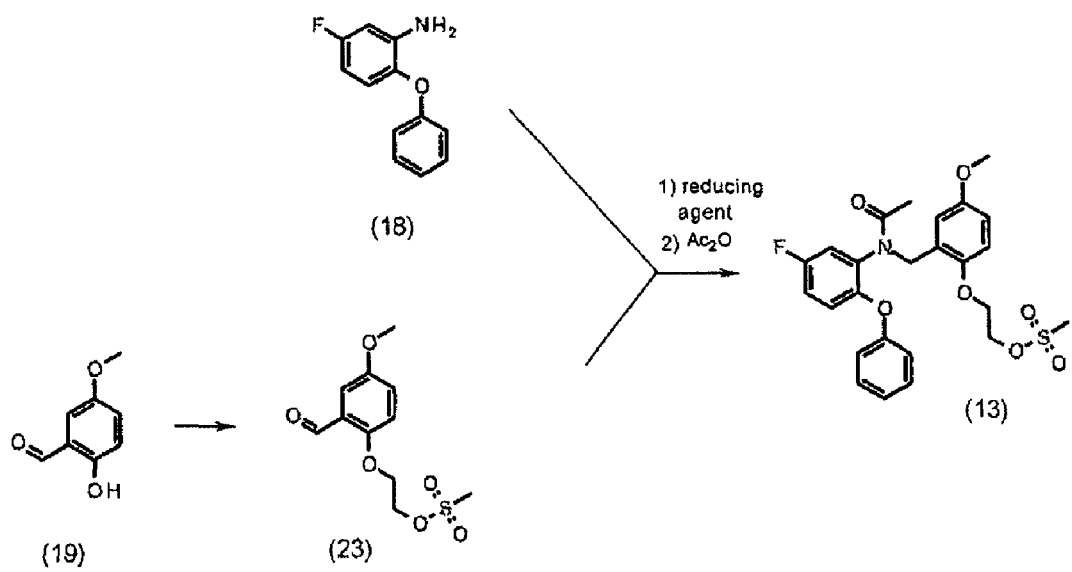
FIG. 16: Depicts a synthetic route for forming a compound of Formula I via the reductive N-alkylation of a compound of formula III and an aldehyde of formula V.

FIG. 16 depicts another synthetic route for forming a compound of Formula I via the reductive N-alkylation of a compound of formula III and an aldehyde of formula V. Aniline 18 (comp. formula V) can be converted in a reductive amination reaction with tris-acetoxy sodium borohydrid and acetic acid in dichloromethane and aldehyde 23 and subsequent acetylation, e.g. with acetic acid anhydride, to obtain the acetylated secondary aniline 13. Other useful reducing agents are well-known to experts: e.g. sodium cyano borohydrid in methanol or hydrogen and heterogenous catalysts (e.g. palladium on carbon (Bioorg. Med. Chem. Lett.; 15; 22; (2005); 4989-4993) or platinum oxide), dibutyl tin chloride and phenyl silane (Org. Lett.; 25; (2005); 5653-5656). Aldehyde 23 is prepared in an alkylation reaction with commercially available phenol 19 and 1,2-bis-methanesulfonyloxy-ethane (J. Med. Chem.; 47; 17; (2004); 4300-4315) by use of potassium carbonate and in dimethylformamide. But also other bases, including but not limited to caesium or sodium carbonate, sodium hydroxid, potassium hydroxid, lithium hydroxid, tetraalkyl hydroxid, sodium hydrid and other solvents, including but not limited to acetone, tetrahydrofuran, eventually mixed with water, are possible.

Figure 17:
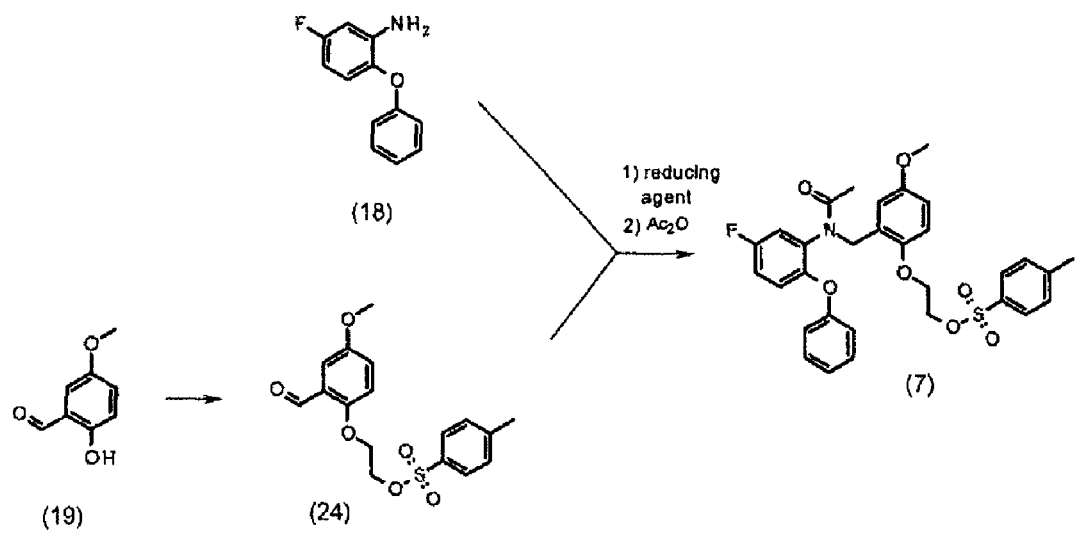
FIG. 17: Depicts a synthetic route for forming compound 7 via the reductive N-alkylation of a compound of formula III and an aldehyde of formula V.

FIG. 17 depicts a very similar synthetic route for forming compound 7 via the reductive N-alkylation of a compound of formula III and an aldehyde of formula V.

Figure 18:
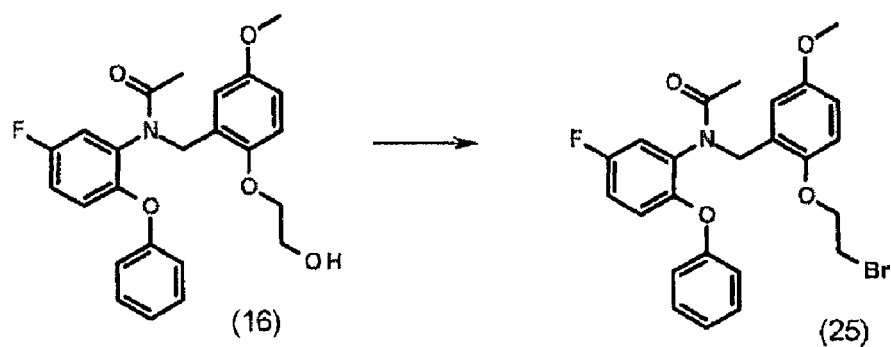
FIG. 18: Depicts a synthetic route for forming a compound of formula I from a compound of formula II.

FIG. 18 depicts another synthetic route for forming a compound of formula I from a compound of formula II whereas bromide 25 is suited as precursor (starting material) for the nucleophilic $^{18}$F-radiofluorination reaction towards compound 3.

Alcohol 16 is converted to the corresponding bromide 25 by methods which are well known to experts. For example alcohol 16 is treated with triphenylphosphin and tetrabromomethane in dichloromethane to obtain bromide 25.

Figure 19:
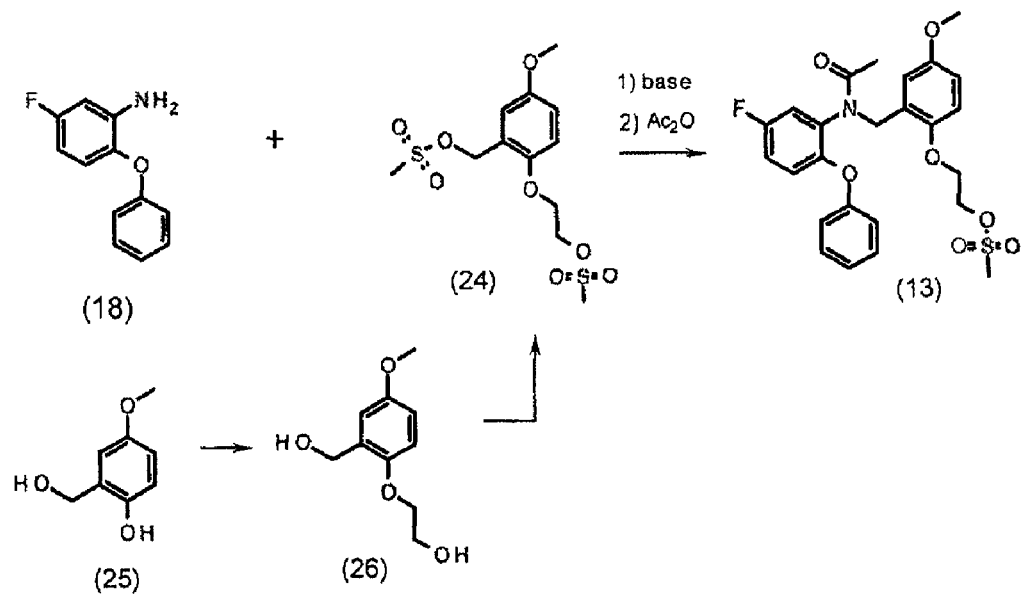
FIG. 19: Depicts an example for a synthetic route for forming a compound of formula I or II by use of a compound of formula V and an electrophile of formula VI and subsequent N-acetylation.

FIG. 19 depicts an example for a synthetic route for forming a compound of formula I or II by use of a compound of formula V and an electrophile of formula VI and subsequent N-acetylation.

Aniline 18 is alkylated by bis-mesylate 24. The alkylation is highly selective due to the more activated benzylic leaving group. Subsequent N-acetylation with acetic acid anhydride or by other acetylating agents which are well-known to experts resulted in compound 13. Bis-mesylate 24 is the product of the mesylation reaction of bis-alcohol 26 by typical methods which are well-known to experts. Bis-alcohol (26) can be prepared from phenol 25 (Rarechem) with 2-chloro-ethanol or another 2-substituted ethanol derivative with a leaving group in 2-postion (e.g. 2-bromo-ethanol; comp. Farmaco Ed. Sci.; 14; (1959); 159, 170 and Tetrahedron; 59; 29; 2003; 5457-5468).

Figure 20:
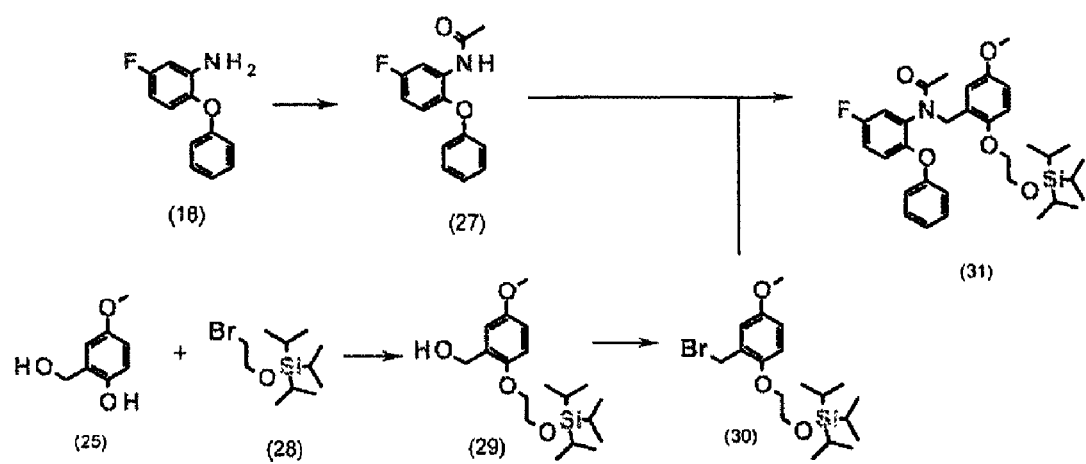
FIG. 20: Depicts an example for the synthetic route for forming a compound of formula I and II by use of a compound of formula VIII and an electrophile of formula VI.

FIG. 20 depicts an example for the synthetic route for forming a compound of formula I and II by use of a compound of formula VIII and an electrophile of formula VI. Compound 18 is acetylated by standard methods using acetanhydride and pyridine. The phenol functionality of compound 25 is alkylated with bromide 28 (J. Med. Chem.; 47; 25; 2004; 6124-6127) using caesium carbonate as base and DMF as solvent. But also other base/solvent combinations are possible including, but not limited to potassium carbonate, sodium carbonate, sodium hydride, tetrahydrofuran and acetonitril. The benzylic alcohol 29 is brominated in an "Appel reaction" to compound 30 with tetra-bromo methane and triphenylphosphine in tetrahydrofuran. Amide 27 is deprotonated with sodium hydride in THF and substituted with bromide 30 to obtain compound 31. The silyl ether 31 can be deprotected towards compound 16 (FIG. 13) using either acid or fluoride anions in e.g. tetrahydrofuran (e.g. analogous to J. Am. Chem. Soc.; 128; 13; 2006; 4356-4364.)"

Experimental Part

"General procedure A (Alkylation of Phenol Derivatives with O-Protected 2-Bromo Ethanols):

To a solution of phenol derivative (30 mmol) in 60 ml dry DMF was added 35 mmol caesium carbonate at 0° C. The reaction mixture was stirred for 30 min. 35 mmol O-protected 2-bromo-ethanol is dissolved in 10 ml DMF is added dropwisly. The reaction mixture is stirred for 10-16 hours at room temperature. The solvent is evaporated and the residue is diluted with ethyl acetate and water. The organic phase is separated. The aqueous phase is extracted three times with ethyl acetate. The combined organic phases were washed with brine, dried with magnesium sulphate and were evaporated. The residue was purified by silica chromatography using ethylacetate/hexane solvent mixtures as gradient.

General Procedure B (Appel Reaction of Benzylic Alcohol Derivatives Towards Corresponding Bromides):

To a cooled 0° C. solution of benzylic alcohol derivative (20 mmol), PPh$_3$ (30 mmol), and CH$_2$Cl$_2$ (500 mL) was added CBr$_4$ (30 mmol) portionwise. The ice bath was removed and the solution stirred overnight. Silica gel was added to the mixture and the solvent removed in vacuo. Flash chromatography (EtOAc/hexanes) afforded the benzyl bromide derivative.

General Procedure C (Alkylation of N-(5-Fluoro-2-phenoxy-phenyl)-acetamide):

To a suspension of 12 mmol sodium hydride in 20 ml dry THF 10 mmol N-(5-Fluoro-2-phenoxy-phenyl)-acetamide which is dissolved in 5 ml dry THF and were added dropwisely at 0° C. The reaction mixture was stirred for 30 min at room temperature. 12 mmol bromide were dissolved in 5 ml dry tetrahydrofuran and were added to the reaction mixture dropwisely at 0° C. The reaction mixture was refluxed for 4 hours. The mixture is cooled to room temperature and poured onto a vigorously stirred diethyl ether-water mixture. The organic phase is separated. The aqueous phase is extracted three times with ethyl acetate. The combined organic phases are washed with brine, dried with magnesium sulphate and are evaporated. The residue is purified by silica chromatography using ethyl acetate/hexane solvent mixtures as gradient.

General Procedure D (Acidic Deprotection of Acid Sensitive Hydroxyl Protecting Groups):

To a solution of 3 mmol hydroxyl-protected compound in 5 ml dioxane is added 3 ml of a 4N HCl solution in dioxane (Aldrich) dropwisly at 0° C. The reaction mixture is stirred at 40° C. for 6 hours. Diethyl ether and saturated sodium hydrogen carbonate solution is added at 0° C. The two-phase mixture is stirred vigorously for 20 min. The organic phase is separated. The aqueous phase is extracted three times with ethyl acetate. The combined organic phases are washed with brine, dried with magnesium sulphate and are evaporated. The residue is purified by silica chromatography using ethyl acetate/hexane solvent mixtures as gradient.

Example 1 a) Synthesis of 5-Methoxy-2-[2-(tetrahydro-pyran-2-yloxy)-ethoxy]-benzaldehyde (1a)

To a vigorously stirred solution of 15,2 g (100 mmol) 2-hydroxy-5-methoxy-benzaldehyde and 42.4 g (130 mmol) caesium carbonate in 350 ml DMF at 0° C. was added 26.1 g (125 mmol) 2-(2-Bromo-ethoxy)-tetrahydro-pyran (J. Org. Chem.; 50; 22; (1985); 4238-4245) in 50 ml DMF dropwisely. The reaction mixture was stirred vigorously at 70° C. for 6 h. The solvent was evaporated. 200 ml water and 200 ml ethyl acetate were added. The organic phase was separated. The aqueous phase was extracted three times with 100 ml ethyl acetate each. The combined organic phases were washed with 50 ml water and 50 ml brine. The organic phase was dried with magnesium sulphate and evaporated. The crude product was purified by silica column chromatography (ethylacetate:hexane 1:3). The desired product 1a was obtained in 81% yield (22.7 g, 81 mmol) as yellow oil.

MS-ESI: 281 (M$^+$1, 100).

| Elementary analysis: | C | 64.27% | H | 5.34% |
|---|---|---|---|---|
| Determined: | C | 64.25% | H | 5.35% | b) Synthesis of 5-fluoro-2-phenoxy-phenylamine (1b)

The atmosphere over a stirred solution of 11,6 g (50 mmol) 4-fluoro-2-nitro-1-phenoxy-benzene and catalytic amount of palladium on carbon in 150 ml iso-propanol at 20° C. was saturated with hydrogen. The reaction mixture was stirred vigorously at 25° C. for 8 h. The reaction mixture was filtered over celite. The filtrate was evaporated. 200 ml water and 200 ml dichloromethane were added. The organic phase was separated. The aqueous phase was extracted three times with 100 ml dichloromethane each. The combined organic phases were washed with 50 ml water and 50 ml brine. The organic phase was dried with magnesium sulfate and evaporated. The crude product 1b was used without purification. The desired crude product 1b was obtained in 94% yield (9.54 g, 47 mmol) as yellow oil.

MS-ESI: 204 (M$^+$+1, 100).

| Elementary analysis: | C | 70.93% | H | 4.96% | F | 9.35% | N | 6.89% |
|---|---|---|---|---|---|---|---|---|
| Determined: | C | 71.00% | H | 4.92% | F | 9.33% | N | 6.87% | c) Synthesis of (5-Fluoro-2-phenoxy-phenyl)-{5-methoxy-2-[2-(tetrahydro-pyran-2-yloxy)-ethoxy]-benzyl}-amine (1c)

To stirred solution of 9.1 g (45 mmol) 1b, 12.6 g (45 mmol) 1a and one drop of glacial acid in 60 ml dichloroethane (pH=5) were added 14.8 g (70 mmol) sodium tris-acetoxy hydro borane. The reaction mixture was stirred over night and diluted with 5 ml water. The pH value was adjusted with aqueous sodium hydroxyd solution to pH=8-9. The mixture was extracted three times with dichloromethane. The combined organic phases were washed with water and brine and were dried with magnesium sulfate. The desired crude product 1e was obtained in 66% yield (13.9 g, 29.7 mmol) as yellow oil. The crude product 1e was used without further purification.

MS-ESI: 468 (M$^+$+1, 89).

d) Synthesis of N-(5-Fluoro-2-phenoxy-phenyl)-N-{5-methoxy-2-[2-(tetrahydro-pyran-2-yl-oxy)-ethoxy]-benzyl}-acetamide (1d)

To a solution of 5.0 g (10.7 mmol) crude 1c in 50 ml ml pyridine was added 4.37 g (42.8 mmol) acetic acid anhydride. The reaction mixture was stirred over night and poured into ice-cold ethyl acetate. The organic phase was washed with water and brine and were dried with magnesium sulfate. The crude product was purified by silica column chromatography (ethyl acetate:hexane gradient 1:8→1:4). The desired product 1d was obtained in 84% yield (4.5 g, 8.9 mmol).

MS-ESI: 510 (M$^+$+1, 100).

| Elementary analysis: | C | 68.36% | H | 6.33% | F | 3.73% | N | 2.75% |
|---|---|---|---|---|---|---|---|---|
| Determined: | C | 68.34% | H | 6.34% | F | 3.71% | N | 2.74% | e) Synthesis of N-(5-Fluoro-2-phenoxy-phenyl)-N-[2-(2-hydroxy-ethoxy)-5-methoxy-benzyl]-acetamide (1e)

To a solution of 1.53 g (3.0 mmol) 1d in 15 ml methanol was added a catalytic amount of tosyl acid. The reaction mixture was stirred for 4 h at 25° C. The reaction mixture was poured in ice-cold ethyl acetate. The solution was washed twice with ice-cold diluted aqueous sodium hydrogen carbonate solution and brine and dried with magnesium sulfate. The crude product was purified by silica column chromatography (ethyl acetate:hexane gradient 1:4-1:2). The desired product 1e was obtained in 71% yield (0.91 g, 2.13 mmol) as yellow oil.

MS-ESI: 426 ($M^+$+1, 100).

| Elementary analysis: | C | 67.75% | H | 5.69% | F | 4.47% | N | 3.29% |
|---|---|---|---|---|---|---|---|---|
| Determined: | C | 67.72% | H | 5.71% | F | 4.46% | N | 3.28% | f) Synthesis of N-(5-Fluoro-2-phenoxy-phenyl)-N-[2-(2-mesyloxy-ethoxy)-5-methoxy-benzyl]-acetamide (1f)

To a solution of 300 mg (0.71 mmol) 1e and 139 mg (1.06 mmol) diisopropyl ethyl amine in 5 ml dichloromethane was added 97 mg (0.85 mmol) mesyl chloride in 0.5 ml dichloromethane drop wisely at −10° C. The stirred reaction mixture was warmed over a period of 4 h to room temperature and diluted with dichloromethane. The organic phase was washed with saturated sodium hydrogen carbonate solution, water and brine. The organic phase was dried with magnesium sulfate. The crude product was purified by silica column chromatography (ethyl acetate:hexane gradient 1:6→1:2). The desired product 1f was obtained in 88% yield (346 mg, 0.62 mmol) as yellow oil.

MS-ESI: 559 ($M^+$+1, 60).

| Elementary analysis: | C | 59.63% | H | 5.20% | F | 3.77% | N | 2.78% |
|---|---|---|---|---|---|---|---|---|
| Determined: | C | 59.62% | H | 5.20% | F | 3.78% | N | 2.77% | g) Synthesis of N-(5-Fluoro-2-phenoxyphenyl)-N-(2-(2-[$^{18}$F]-fluoro-ethoxy)-5-methoxybenzyl)acetamide (1 g)

To a Wheaton vial (5 ml) charged with 2.5 mg Kryptofix 222 in 0.75 ml acetonitrile and 0.5 mg potassium carbonate and the fluorine containing water (2.2 GBq, 250 µl) was added. The solvent was removed by heating at 120° C. for 10 mins under a stream of nitrogen. Anhydrous MeCN (1 ml) is added and evaporated as before. This step is repeated again. A solution of 1 g (2 mg) in 0.705 ml anhydrous DMF is added. After heating at 130° C. for 30 min. The crude reaction mixture is analyzed using an analytical HPLC: ACE3-C18 50 mm*4,6 mm; solvent: 5% acetonitril-95% acetonitril in water in 7 min., flow: 2 ml/min. The F-18 labeled product 1 g is confirmed by co-injection with the non-radioactive F-19 fluoro standard on the analytical HPLC. The crude product (160 MBq) was purified by preparative HPLC column: ACES-C18-HL 250 mm*10 mm; solvent 62% acetonitril-38% water, isocratic 20 min., flow: 3 ml/min. The desired product 1 g was obtained (45 MBq) as reconfirmed by co-injection with the non-radioactive F-19 fluoro standard on the analytical HPLC.

Example 2 a) Synthesis of 2-(2-Benzyloxy-ethoxy)-5-methoxy-benzaldehyde (2a)

To a vigorously stirred solution of 15,2 g (100 mmol) 2-hydroxy-5-methoxy-benzaldehyde and 42.4 g (130 mmol) caesium carbonate in 350 ml DMF at 0° C. was added 26.9 g (125 mmol) (2-Bromo-ethoxymethyl)-benzene (Adrich) in 50 ml DMF dropwisely. The reaction mixture was stirred vigorously at 70° C. for 6 h. The solvent was evaporated. 200 ml water and 200 ml ethyl acetate were added. The organic phase was separated. The aqueous phase was extracted three times with 100 ml ethyl acetate each. The combined organic phases were washed with 50 ml water and 50 ml brine. The organic phase was dried with magnesium sulphate and evaporated. The crude product was purified by silica column chromatography (gradient ethylacetate:hexane 1:3→1:2). The desired product 2a was obtained in 86% yield (24.6 g, 86 mmol) as yellow oil.

MS-ESI: 287 ($M^+$+1, 100).

| Elementary analysis: | C | 71.31% | H | 6.34% |
|---|---|---|---|---|
| Determined: | C | 71.29% | H | 6.35% | b) Synthesis of [2-(2-benzyloxy-ethoxy)-5-methoxy-benzyl]-(5-fluoro-2-phenoxy-phenyl)-amine (2b)

To stirred solution of 4.6 g (23 mmol) 1b, 6.3 g (23 mmol) 2a and one drop of glacial acid in 35 ml dichloroethane (pH=5) were added 7.4 g (35 mmol) sodium tris-acetoxy hydro borane. The reaction mixture was stirred over night and diluted with 3 ml water. The pH value was adjusted with aqueous sodium hydroxyd solution to pH=8-9. The mixture was extracted three times with dichloromethane. The combined organic phases were washed with water and brine and were dried with magnesium sulfate. The desired crude product 2b was obtained in 78% yield (8.5 g, 17.9 mmol) as yellow oil. The crude product 2b was used without further purification.

MS-ESI: 475 ($M^+$+1, 81).

c) Synthesis of N-[2-(2-benzyloxy-ethoxy)-5-methoxy-benzyl]-N-(5-fluoro-2-phenoxy-phenyl)-acetamide (2c)

To a solution of 5.08 g (10.7 mmol) crude 2b in 50 ml ml pyridine was added 4.37 g (42.8 mmol) acetic acid anhydride. The reaction mixture was stirred over night and poured into ice-cold ethyl acetate. The organic phase was washed with water, diluted aqueous sodium hydrogen sulfate, water and brine and were dried with magnesium sulfate. The crude product was purified by silica column chromatography (ethyl acetate:hexane gradient 1:8→1:4). The desired product 2c was obtained in 79% yield (4.36 g, 8.45 mmol).

MS-ESI: 517 (M$^+$+1, 100).

| Elementary analysis: | C | 72.22% | H | 5.86% | F | 3.68% | N | 2.72% |
|---|---|---|---|---|---|---|---|---|
| Determined: | C | 72.20% | H | 5.87% | F | 3.67% | N | 2.71% | d) Synthesis of N-(5-Fluoro-2-phenoxy-phenyl)-N-(2-hydroxy-5-methoxy-benzyl)-acetamide (2d)

The atmosphere over a stirred solution of 2.58 g (5 mmol) 4-fluoro-2-nitro-1-phenoxy-benzene with 5-methoxy-2-hydroxy-1-tosyloxy-phenyl and catalytic amount of palladium on carbon in 35 ml iso-propanol at 20° C. was saturated with hydrogen. The reaction mixture was stirred vigorously at 25° C. for 7 h. The reaction mixture was filtered over celite. The solvent of the filtrate was evaporated. 10 ml water and 10 ml dichloromethane were added. The organic phase was separated. The aqueous phase was extracted three times with 10 ml dichloromethane each. The combined organic phases were washed with 10 ml water and 10 ml brine. The organic phase was dried with magnesium sulfate and evaporated. The crude product 2d was used without purification. The desired crude product 2d was obtained in 89% yield (1.7 g, 4.45 mmol) as yellow oil.

MS-ESI: 382 (M$^+$+1, 100).

| Elementary analysis: | C | 69.28% | H | 5.29% | F | 4.98% | N | 3.67% |
|---|---|---|---|---|---|---|---|---|
| Determined: | C | 69.25% | H | 5.30% | F | 4.97% | N | 3.66% |

Example 3 a) Synthesis of N-(5-Fluoro-2-phenoxyphenyl)-N-[2-(2-mesyloxy-ethoxy)-5-methoxy benzyl]acetamide (3a) corresponding to compound 4c or 13

To a vigorously stirred solution of 38.1 g (100 mmol) N-(5-fluoro-2-phenoxy-phenyl)-N-(2-hydroxy-5-methoxy-benzyl)-acetamide (Biorg. Med. Chem., (2004), 12, 423) and 42.4 g (130 mmol) caesium carbonate in 350 ml DMF at 0° C. was added 27,3 g (125 mmol) 1,2-bis-methanesulfonyloxy-ethane ((J. Med. Chem.; 47; 17; (2004); 4300-4315)) in 50 ml DMF dropwisely. The reaction mixture was stirred vigorously at 70° C. for 6,5 h. The solvent was evaporated. 200 ml water and 200 ml ethyl acetate were added. The organic phase was separated. The aqueous phase was extracted three times with 100 ml ethyl acetate each. The combined organic phases were washed with 50 ml water and 50 ml brine. The organic phase was dried with magnesium sulfate and evaporated. The crude product was purified by silica column chromatography (gradient ethylacetate:hexane 1:6→1:2). The desired product 3a was obtained in 85% yield (42.8 g, 85 mmol) as yellow oil.

MS-ESI: 505 (M$^+$+1, 78).

| Elementary analysis: | C | 59.63% | H | 5.20% | F | 3.77% | N | 2.78% |
|---|---|---|---|---|---|---|---|---|
| Determined: | C | 59.62% | H | 5.21% | F | 3.76% | N | 2.78% |

Example 4 a) Synthesis of 5-methoxy-2-(2-mesyloxyethoxy)-benzaldehyd (4a)

To a vigorously stirred solution of 15,2 g (100 mmol) 2-hydroxy-5-methoxy-benzaldehyde and 42.4 g (130 mmol) caesium carbonate in 350 ml DMF at 0° C. was added 27,3 g (125 mmol) 1,2-bis-methanesulfonyloxy-ethane ((J. Med. Chem.; 47; 17; (2004); 4300-4315) in 50 ml DMF dropwisely. The reaction mixture was stirred vigorously at 70° C. for 5 h. The solvent was evaporated. 200 ml water and 200 ml ethyl acetate were added. The organic phase was separated. The aqueous phase was extracted three times with 100 ml ethyl acetate each. The combined organic phases were washed with 50 ml water and 50 ml brine. The organic phase was dried with magnesium sulfate and evaporated. The crude product was purified by silica column chromatography (gradient ethylacetate:hexane 1:6, ethyl acetate→1:2). The desired product 4a was obtained in 78% yield (21.4 g, 78 mmol) as yellow oil.

MS-ESI: 275 (M$^+$+1, 100).

| Elementary analysis: | C | 48.17% | H | 5.14% |
|---|---|---|---|---|
| Determined: | C | 48.19% | H | 5.15% | b) Synthesis of (5-Fluoro-2-phenoxy-phenyl)-{5-methoxy-2-[2-(mesyloxy-)-ethoxy]-benzyl}-amine (4b)

To stirred solution of 9.1 g (45 mmol) 1b, 12.3 g (45 mmol) 4a and one drop of glacial acid in 60 ml dichloroethane (pH=5) were added 14.8 g (70 mmol) sodium tris-acetoxy hydro borane. The reaction mixture was stirred over night and diluted with 5 ml water. The pH value was adjusted with aqueous sodium hydroxyd solution to pH=8-9. The mixture was extracted three times with dichloromethane. The combined organic phases were washed with water and brine and were dried with magnesium sulfate. The desired crude product 4b was obtained in 62% yield (12.9 g, 27.9 mmol) as yellow oil. The crude product 4b was used without further purification.

MS-ESI: 463 (M$^+$+1, 65).

c) N-(5-Fluoro-2-phenoxy-phenyl)-N-[2-(2-mesyloxy-ethoxy)-5-methoxy-benzyl]-acetamide (4c) Corresponding to Compound 3a or 13

To a solution of 4.94 g (10.7 mmol) crude 4b in 50 ml ml pyridine was added 4.37 g (418 mmol) acetic acid anhydride. The reaction mixture was stirred over night and poured into ice-cold ethyl acetate. The organic phase was washed with water and brine and were dried with magnesium sulfate. The crude product was purified by silica column chromatography (ethyl acetate:hexane gradient 1:8→1:4). The desired product 4c was obtained in 80% yield (4.3 g, 8.56 mmol).

MS-ESI: 504 (M$^+$+1, 78).

| Elementary analysis: | C | 59.63% | H | 5.20% | F | 3.77% | N | 2.78% |
|---|---|---|---|---|---|---|---|---|
| Determined: | C | 59.61% | H | 5.19% | F | 3.79% | N | 2.77% |

Example 5 a) Synthesis of 5-methoxy-2-(2-tosyloxy-ethoxy)-benzaldehyd (5a)

To a vigorously stirred solution of 15,2 g (100 mmol) 2-hydroxy-5-methoxy-benzaldehyde and 42.4 g (130 mmol) caesium carbonate in 350 ml DMF at 0° C. was added 46.3 g (125 mmol) ethylene glycol bis-toluene sulfonate (Aldrich) in 50 ml DMF dropwisely. The reaction mixture was stirred vigorously at 70° C. for 5 h. The solvent was evaporated. 200 ml water and 200 ml ethyl acetate were added. The organic phase was separated. The aqueous phase was extracted three times with 100 ml ethyl acetate each. The combined organic phases were washed with 50 ml water and 50 ml brine. The organic phase was dried with magnesium sulfate and evaporated. The crude product was purified by silica column chromatography (gradient ethylacetate:hexane 1:6, ethyl acetate→1:2). The desired product 5a was obtained in 75% yield (26.3 g, 75 mmol) as yellow oil.

MS-ESI: 351 ($M^+$+1, 100).

| Elementary analysis: | C | 58.27% | H | 5.18% |
|---|---|---|---|---|
| Determined: | C | 58.27% | H | 5.17% | b) Synthesis of (5-Fluoro-2-phenoxy-phenyl)-{5-methoxy-2-[2-(tosyloxy-)-ethoxy]-benzyl}-amine (5b)

To stirred solution of 9.1 g (45 mmol) 1b, 15.8 g (45 mmol) 5a and one drop of glacial acid in 60 ml dichloroethane (pH=5) were added 14.8 g (70 mmol) sodium tris-acetoxy hydro borane. The reaction mixture was stirred over night and diluted with 5 ml water. The pH value was adjusted with aqueous sodium hydroxyd solution to pH=8-9. The mixture was extracted three times with dichloromethane. The combined organic phases were washed with water and brine and were dried with magnesium sulfate. The desired crude product 5b was obtained in 71% yield (17.2 g, 32.0 mmol) as yellow oil. The crude product 5b was used without further purification.

MS-ESI: 539 ($M^+$+1, 64).

c) Synthesis of N-(5-Fluoro-2-phenoxy-phenyl)-N-[2-(2-tosyloxy-ethoxy)-5-methoxy-benzyl]-acetamide (5c)

To a solution of 5.75 g (10.7 mmol) crude 5b in 50 ml pyridine was added 4.37 g (42.8 mmol) acetic acid anhydride. The reaction mixture was stirred over night and poured into ice-cold ethyl acetate. The organic phase was washed with water and brine and were dried with magnesium sulfate. The crude product was purified by silica column chromatography (ethyl acetate:hexane gradient 1:8→1:4). The desired product 5c was obtained in 74.5% yield (4.62 g, 7.97 mmol).

MS-ESI: 581 ($M^+$+1, 100).

| Elementary analysis: | C | 64.24% | H | 5.22% | F | 3.28% | N | 2.42% |
|---|---|---|---|---|---|---|---|---|
| Determined: | C | 64.22% | H | 5.23% | F | 3.26% | N | 2.41% |

Example 6 a) Synthesis of N-(5-Fluoro-2-phenoxy-phenyl)-N[2-(2-bromo-ethoxy)-5-methoxy-benzyl]-acetamide (6a)

To a stirred solution of 1.69 g (5.1 mmol) $CBr_4$ and 2.89 g (11 mmol) $PPh_3$ in dry dichloromethane (35 mL) 2.04 g (4.8 mmol) (1e) was added at 0° C. The reaction mixture was allowed to warm to room temperature and stirred overnight, then diluted with ether and filtered through sintered funnel. The filtrate was concentrated and the residue was purified by silica column chromatography (gradient hexane-ethyl acetate 6:1→2:1). The desired product 6a was obtained in 64% yield (1.37 g, 3.07 mmol).

MS-ESI: 446 ($M^{Br79}$+1, 100).

| Elementary analysis: | C | 59.21% | H | 4.74% | F | 4.26% | N | 3.14% |
|---|---|---|---|---|---|---|---|---|
| Determined: | C | 59.20% | H | 4.74% | F | 4.25% | N | 3.13% |

Example 7 a) Synthesis of 2-(2-hydroxymethyl-4-methoxy-phenoxy)-ethanol

To a stirred solution of 7.7 g (50 mmol) 2-hydroxymethyl-4-methoxy-phenol (Rarechem) and 4.0 g (100 mmol) sodium hydroxyd in 300 ml ethanol and 150 ml water 5.6 g (70 mmol) 2-chloro ethanol were added at 0° C. The reaction mixture was stirred vigorously over night at 70° C. The reaction mixture was cooled to 0° C. and neutralized by use of 3N HCl to pH The volume of the mixture was reduced to a fifth of the volume. Dichloromethane was added to the residue. The mixture was filtered and the filtrate was diluted with 150 ml water and 150 ml dichloromethane. The organic phase was separated. The aqueous phase was extracted three times with 200 ml dichloromethane. The combined organic phases were washed with 50 ml water and 50 ml brine. The organic phase was dried with magnesium sulfate and evaporated. The crude product was purified by silica column chromatography (gradient hexane:ethyl acetate 1:1→hexane:ethyl acetate: methanol 1:10:0.1). The desired product 7a was obtained in 65% yield (6.44 g; 32.5 mmol).

MS-ESI: 199 ($M^+$+1, 100).

| Elementary analysis: | C | 60.59% | H | 7.12% |
|---|---|---|---|---|
| Determined: | C | 64.22% | H | 5.23% | b) Synthesis of Methanesulfonic acid 2-(2-methanesulfonyloxy-ethoxy)-5-methoxy-benzyl ester To a solution of 6.41 g (32.3 mmol) 7a and 13.9 g (106 mmol) diisopropyl ethyl amine in 25 ml dichloromethane was added 9.7 g (85 mmol) mesyl chloride in 5 ml dichloromethane drop wisely at −10° C. The stirred reaction mixture was warmed over a period of 4 h to room temperature and diluted with dichloromethane. The organic phase was washed with saturated sodium hydrogen carbonate solution, water and brine. The organic phase was dried with magnesium sulfate. The crude product was purified by silica column chromatography (ethyl acetate:hexane gradient 1:4→1:1). The desired product 7b was obtained in 72% yield (8.25 g, 23.3 mmol) as yellow oil.

MS-ESI: 355 ($M^4$+1, 100).

| Elementary analysis: | C | 40.67% | H | 5.12% |
|---|---|---|---|---|
| Determined: | C | 40.70% | H | 5.13% | c) Synthesis of N-(5-fluoro-2-phenoxy-phenyl)-N-[2-(2-mesyloxy-ethoxy)-5-methoxy-benzyl]-acetamide (7c)

To a solution of 1.01 g (5 mmol) 1b and 4.24 g (13.0 mmol) caesium carbonate in 50 ml DMF at 0° C. was added 531 mg (1.5 mmol) 7b in 2 ml DMF dropwisely. The reaction mixture was stirred vigorously at 70° C. for 5 h. The solvent was evaporated. 50 ml water and 50 ml ethyl acetate were added. The organic phase was separated. The aqueous phase was extracted three times with 50 ml ethyl acetate each. The combined organic phases were washed with 10 ml water and 10 ml brine. The organic phase was dried with magnesium sulfate and evaporated. The crude product diluted in 5 ml pyridine. 2.17 g (21.0 mmol) acetic acid anhydride were added. The reaction mixture was stirred over night and poured into ice-cold ethyl acetate. The organic phase was washed with water and brine and were dried with magnesium sulfate. The crude product was purified by silica column chromatography (ethyl acetate:hexane gradient 1:8→1:4). The desired product 7c was obtained in 72% yield (543 mg, 1.08 mmol) as yellow oil.

MS-ESI: 504 ($M^+$+1, 89).

| Elementary analysis: | C | 59.63% | H | 5.20% | F | 3.77% | N | 2.78% |
|---|---|---|---|---|---|---|---|---|
| Determined: | C | 59.61% | H | 5.21% | F | 3.77% | N | 2.78% |

Example 8 a) Synthesis of N-(5-Fluoro-2-phenoxyphenyl)-N-(2-(2-[$^{18}$F]fluoroethoxy)-5-methoxybenzyl)acetamide (8a) via compound 7

To a Wheaton vial (5 ml) charged with 2.5 mg Kryptofix 222 in 0.75 ml acetonitrile and 0.5 mg potassium carbonate and the fluorine containing water (2.5 GN, 2500) was added. The solvent was removed by heating at 120° C. for 10 mins under a stream of nitrogen. Anhydrous MeCN (1 ml) is added and evaporated as before. This step is repeated again. A solution of 7 (2 mg) in 0.705 ml anhydrous DMF is added. After heating at 130° C. for 30 min. The crude reaction mixture is analyzed using an analytical HPLC: ACE3-C18 50 mm*4,6 mm; solvent: 5% acetonitril—95% acetonitril in water in 7 min., flow: 2 ml/min. The F-18 labeled product 1 g is confirmed by co-injection with the non-radioactive F-19 fluoro standard on the analytical HPLC. The crude product (221 MBq) was purified by preparative HPLC column: ACES-C18-HL 250 mm*10 mm; solvent 62% acetonitril-38% water, isocratic 20 min., flow: 3 ml/min. The desired product 1 g was obtained (55 MBq) as reconfirmed by co-injection with the non-radioactive F-19 fluoro standard on the analytical HPLC.

Example 9 a) Synthesis of 5-Methoxy-2-(2-triisopropylsilanyloxy-ethoxy)phenyl]-methanol The general procedure A was applied to (2-Bromoethoxy)-triisopropyl-silane (J. Med. Chem.; 47; 25; 2004; 6124-6127) and 2-hydroxymethyl-4-methoxy-phenol (Aldrich). The desired compound 9a was obtained in 87% yield.

MS-ESI: 355 ($M^+$+1, 100).

| Elementary analysis: | C | 64.36% | H | 9.67% |
|---|---|---|---|---|
| Determined: | C | 64.38% | H | 9.68% | b) Synthesis of [2-(2-Bromomethyl-4-methoxy-phenoxy)-ethoxy]-triisopropyl-silane (9b)

The general procedure B was applied to 9a. The desired compound 9b was obtained in 73% yield (14.6 mmol; 6.07 g).

MS-ESI: 418 ($M^+$+1, 100).

| Elementary analysis: | C | 54.67% | H | 7.97% |
|---|---|---|---|---|
| Determined: | C | 54.68% | H | 7.96% | c) Synthesis of N-(5-Fluoro-2-phenoxy-phenyl)-N-[5-methoxy-2-(2-triisopropylsilanyloxy-ethoxy)-benzyl]-acetamide (9c)

The general procedure C was applied to N-(5-Fluoro-2-phenoxy-phenyl)-acetamide and 9b. The desired compound 9c was obtained in 56% yield (3.27 g; 5.61 mmol).

MS-ESI: 583 ($M^+$+1, 100).

| Elementary analysis: | C | 68.13% | H | 7.62% |
|---|---|---|---|---|
| Determined: | C | 68.14% | H | 7.63% | d) Synthesis of 1e from 9c

The general procedure D was applied to 9c. The desired compound 1e was obtained in 89% yield (2.67 mmol, 1.14 g).

MS-EST: 426 ($M^+$+1, 100).

| Elementary analysis: | C | 67.75% | H | 5.69% | N | 3.29% |
|---|---|---|---|---|---|---|
| Determined: | C | 67.74% | H | 5.70% | N | 3.29% |

Example 10 a) Synthesis of 2-(2-Allyloxy-ethoxy)-5-methoxyphenyl]-methanol (10a)

The general procedure A was applied to 3-(2-Bromoethoxy)-propene (Chem. Soc. Jpn.; 55; 5; 1982; 1498-1503) and 2-hydroxymethyl-4-methoxy-phenol (Aldrich). The desired compound 10a was obtained in 75% yield (22.5 mmol; 5,4 g).

MS-ESI: 239 ($M^+$+1, 100).

| Elementary analysis: | C | 65.53% | H | 7.61% |
| --- | --- | --- | --- | --- |
| Determined: | C | 65.54% | H | 7.60% | b) Synthesis of 1-(2-Allyloxy-ethoxy)-2-bromom-ethyl-4-methoxy-benzene (10b)

The general procedure B was applied to 10a. The desired compound 10b was obtained in 67% yield (13.4 mmol; 4.03 g).
MS-ESL 301/303 (M$^+$+1, 80).

| Elementary analysis: | C | 51.84% | H | 5.69% |
| --- | --- | --- | --- | --- |
| Determined: | C | 51.83% | H | 5.70% | c) Synthesis of N-[2-(2-Allyloxy-ethoxy)-5-methoxy-benzyl]-N-(5-fluoro-2-phenoxy-phenyl)-acetamide (10e)

The general procedure C was applied to N-(5-Fluoro-2-phenoxy-phenyl)-acetamide and 10b The desired product 10c was obtained in 49% yield (4.9 mmol; 2.28 g).
MS-ESL 467 (M$^+$1, 80).

| Elementary analysis: | C | 69.66% | H | 6.06% |
| --- | --- | --- | --- | --- |
| Determined: | C | 69.64% | H | 6.07% | d) Synthesis of 1e from 10e (10d)

According to slightly modified protocol from Syn. Lett. (2003), 1061-1063a solution of 2 mmol (932 mg) 10c and 4 mmol N,N-dimethyl barbituric acid in 10 ml tetrahydrofuran was added 0,04 mmol tetrakis(triphenylphosphin)palladium. The reaction mixture was refluxed over night. Diethyl ether and saturated sodium hydrogen carbonate solution was added at 0° C. The two-phase mixture was stirred vigorously for 20 min. The organic phase was separated. The aqueous phase was extracted three times with ethyl acetate. The combined organic phases were washed with brine, dried with magnesium sulphate and were evaporated. The residue was purified by silica chromatography using ethyl acetate/hexane solvent mixtures as gradient. The desired compound 1e was obtained in 84% yield (710 mg, 1.68 mmol).
MS-ESI: 426 (M$^+$1, 100).

| Elementary analysis: | C | 67.75% | H | 5.69% | N | 3.29% |
| --- | --- | --- | --- | --- | --- | --- |
| Determined: | C | 67.72% | H | 5.71% | N | 3.28% | e) Synthesis of Trifluoro-methanesulfonic acid 2-(2-{[acetyl-(5-fluoro-2-phenoxy-phenyl)amino]-methyl}-4-methoxy-phenoxy)-ethyl ester (10e)

To a solution of 426 mg (1 mmol) and 400 mg (5 mmol) pyridine in 6 ml dry dichloromethane was added dropwisely 423 mg (1,5 mmol) trifluorosulphonic acid anhydride at −10° C. The reaction mixture was stirred for 6 h and poured onto a vigorously stirred diethyl ether-water mixture. The organic phase was separated. The aqueous phase was extracted three times with diethyl ether. The combined organic phases were washed with brine, dried with magnesium sulphate and were evaporated. The residue was purified by silica chromatography using ethyl acetate/hexane solvent mixtures as gradient. The desired compound 10e was obtained in 77% yield (430 mg, 0.77 mmol).
MS-EST: 426 (M$^+$+1, 100).

| Elementary analysis: | C | 53.86% | H | 4.16% | N | 2.51% |
| --- | --- | --- | --- | --- | --- | --- |
| Determined: | C | 53.88% | H | 4.17% | N | 2.51% |

The invention claimed is:

1. A compound of formula I:

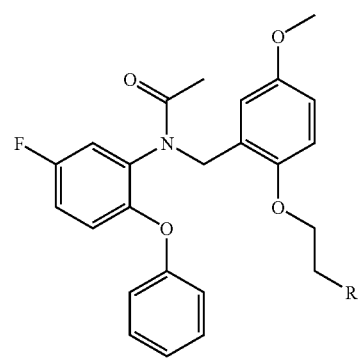

I wherein
R is
  a) —OS(O)$_2$-L
and wherein L is
  a) methyl
  b) trifluormethyl
  c) nonafluorobutyl
  d) $C_1$-$C_6$ alkyl-phenyl
  e)
  f) (2,4,6-$C_1$-$C_6$ tri-alkyl)-phenyl
  g) nitro-phenyl or
  h) halo-phenyl
with the proviso that L is not (para-methyl)-phenyl.

2. The compound according to claim 1, wherein
L is
  a) methyl
  b) trifluormethyl or
  c) nonafluorobutyl.

3. The compound represented by the following structure:

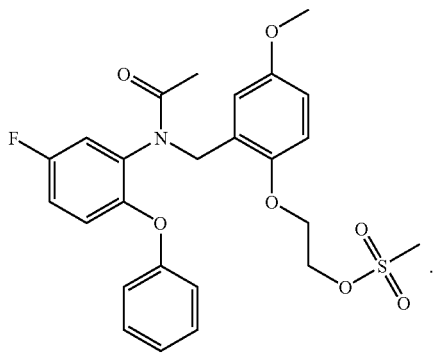

4. A process of preparing compound 3

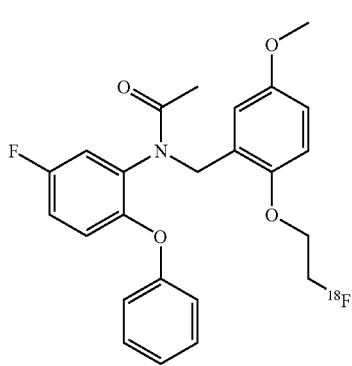

comprising reacting a compound of formula I, as defined in claim 1 with $^{18}$F anions at temperatures in the range of from 50° C. to 160° C.

5. The process according to claim 4, wherein the reaction with $^{18}$F anions is conducted over a period in the range of from 1 to 60 minutes.

6. A process of preparing compound 3

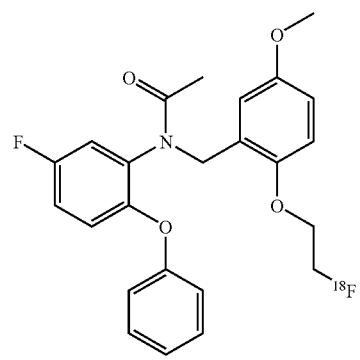

comprising reacting the compound of claim 3 with $^{18}$F anions, at temperatures in the range of from 121° C. to 160° C., and, optionally, upon obtainment of compound 3, adding acid.

* * * * *

UNITED STATES PATENT AND TRADEMARK OFFICE
CERTIFICATE OF CORRECTION

PATENT NO. : 7,803,960 B2
APPLICATION NO. : 11/896607
DATED : September 28, 2010
INVENTOR(S) : Lehmann et al.

It is certified that error appears in the above-identified patent and that said Letters Patent is hereby corrected as shown below:

Column 30, line 55 delete "e)"

Column 30, line 56 reads, "f) (2,4,6-$C_1$–$C_6$ tri-alkyl)-phenyl" SHOULD READ -- e) (2,4,6-$C_1$–$C_6$ tri-alkyl)-phenyl --

Column 30, line 57 reads, "g) nitro-phenyl or" SHOULD READ -- f) nitro-phenyl or --

Column 30, line 58 reads, "h) halo-phenyl" SHOULD READ -- g) halo-phenyl --

Signed and Sealed this

Twenty-first Day of December, 2010

David J. Kappos
*Director of the United States Patent and Trademark Office*